(12) United States Patent
Boamah et al.

(10) Patent No.: US 12,097,015 B2
(45) Date of Patent: Sep. 24, 2024

(54) LIQUID FLOW INDUCED POWER GENERATION USING NANOSCALE METAL LAYERS

(71) Applicants: Northwestern University, Evanston, IL (US); CALIFORNIA INSTITUTE OF TECHNOLOGY, Pasadena, CA (US)

(72) Inventors: Mavis D. Boamah, Evanston, IL (US); Franz M. Geiger, Evanston, IL (US); Thomas F. Miller, III, South Pasadena, CA (US); Jeongmin Kim, Pasadena, CA (US)

(73) Assignees: Northwestern University, Evanston, IL (US); California Institute of Technology, Pasadena, CA (US)

( * ) Notice: Subject to any disclaimer, the term of this patent is extended or adjusted under 35 U.S.C. 154(b) by 734 days.

(21) Appl. No.: 17/276,684

(22) PCT Filed: Sep. 17, 2019

(86) PCT No.: PCT/US2019/051421
§ 371 (c)(1),
(2) Date: Mar. 16, 2021

(87) PCT Pub. No.: WO2020/123005
PCT Pub. Date: Jun. 18, 2020

(65) Prior Publication Data
US 2022/0038032 A1 Feb. 3, 2022

Related U.S. Application Data

(60) Provisional application No. 62/732,822, filed on Sep. 18, 2018, provisional application No. 62/772,319, (Continued)

(51) Int. Cl.
*H02N 1/08* (2006.01)
*A61B 5/026* (2006.01)
*H02N 11/00* (2006.01)

(52) U.S. Cl.
CPC ............... *A61B 5/026* (2013.01); *H02N 1/08* (2013.01); *H02N 11/002* (2013.01)

(58) Field of Classification Search
CPC ........ A61B 5/026; H02N 1/08; H02N 11/002; B82B 1/008; C23C 14/08
See application file for complete search history.

(56) References Cited

U.S. PATENT DOCUMENTS 6,008,625 A * 12/1999 Gan ........................ H01M 6/16
320/135
6,791,205 B2 * 9/2004 Woodbridge ....... F03B 13/1845
441/16

(Continued)

OTHER PUBLICATIONS

Boamah et al., "Dendritic Oxide Growth in Zero-Valent Iron Nanofilms Revealed by Atom Probe," Department of Chemistry, Northwestern University, Evanston, IL 60208, pp. 1-33.

(Continued)

*Primary Examiner* — Alexander Usyatinsky
(74) *Attorney, Agent, or Firm* — Bell & Manning, LLC

(57) ABSTRACT

Energy harvesting devices and methods for converting the mechanical energy of a flowing ionic solution, such as rainwater or seawater, into electric energy are provided. The energy harvesting devices include an electric current generating device that includes a metal layer and an amphoteric metal oxide film disposed over a surface of the metal layer. By moving an electric double layer across the surface of the amphoteric metal oxide film, an electric current is generated in the metal layer.

10 Claims, 29 Drawing Sheets

Related U.S. Application Data filed on Nov. 28, 2018, provisional application No. 62/879,923, filed on Jul. 29, 2019.

(56) References Cited

U.S. PATENT DOCUMENTS

| | | | |
|---|---|---|---|
| 9,738,966 | B2 | 8/2017 | Geiger et al. |
| 2005/0277839 | A1* | 12/2005 | Alderman ............ A61B 5/0031 600/481 |
| 2010/0171394 | A1* | 7/2010 | Glenn ...................... H02N 2/18 310/339 |
| 2013/0026409 | A1* | 1/2013 | Baker .................... H01G 11/64 429/479 |
| 2015/0124311 | A1 | 5/2015 | Parrot |
| 2016/0068944 | A1 | 3/2016 | Geiger et al. |
| 2016/0324435 | A1 | 11/2016 | Kuzum et al. |
| 2018/0183038 | A1 | 6/2018 | Yao et al. |

OTHER PUBLICATIONS

Paul E. Ohno et al., « Phase-referenced nonlinear spectroscopy of the α-quartz/water interface, Nature Communications, vol. 7, Published Dec. 13, 2016, DOI: 10.1038/ncomms13587, pp. 1-5.

The International Search Report and the Written Opinion issued in International Patent Application No. PCT/US19/51412 on Jun. 8, 2020, pp. 1-8.

Boamah et al., "Energy conversion via metal nanolayers," Proceedings of the National Academy of Sciences, vol. 116, No. 33, Aug. 13, 2019, pp. 1620-16215.

Kim et al., "Ion specificity on electric energy generated by flowing water droplet," Angewandte Chemie International Edition, vol. 57, No. 8, Feb. 19, 2018, pp. 2091-2095.

Li et al., "Hydroelectric generator from transparent flexible zinc oxide nanofilms," Nano Energy, vol. 32, 2017, pp. 125-129.

Park et al., "Identification of droplet-flow-induced electric energy on electro-lyte-insulator-semiconductor structure," Journal of the American Chemical Society, vol. 139, No. 32, Aug. 16, 2017, pp. 10968-10971.

The International Search Report and the Written Opinion issued in International Patent Application No. PCT/US19/51421 on Jul. 9, 2020, pp. 1-14.

Wikipedia. "Vanadium(V) Oxide." Wikipedia, Wikimedia Foundation (May 9, 2018).

Jun Yin et al., "Generating electricity by moving a droplet of ionic liquid along graphene," Nature Nanotechnology, vol. 9, May 2014, pp. 377-383.

Shanshan Yang et al., "Mechanism of Electric Power Generation from Ionic Droplet Motion on Polymer Supported Graphene," *Institute of Nanoscience, Nanjing University of Aeronautics and Astronautics, Nanjing 210016, China. Department of Physics, University of California, Berkeley, CA 94720, United States*, pp. 1-21.

D. H. Huynh et al., "Environmentally friendly power generator based on moving liquid dielectric and double layer effect," ScieSB0tific reports, vol. 6, 26708, pp. 1-20. DOI: 10.1038/srep26708.

* cited by examiner

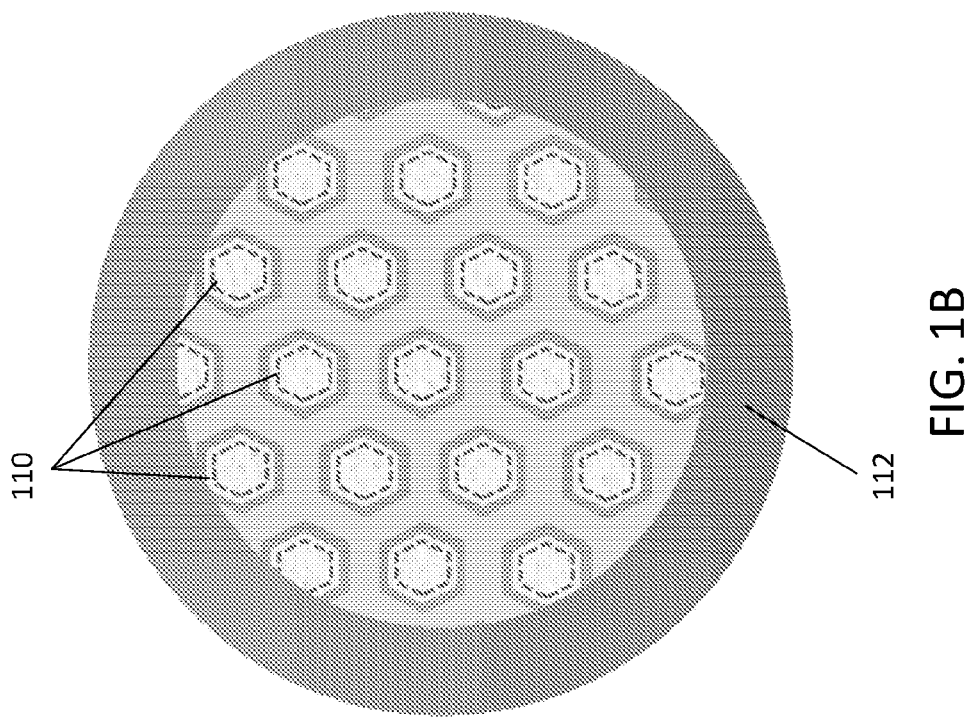
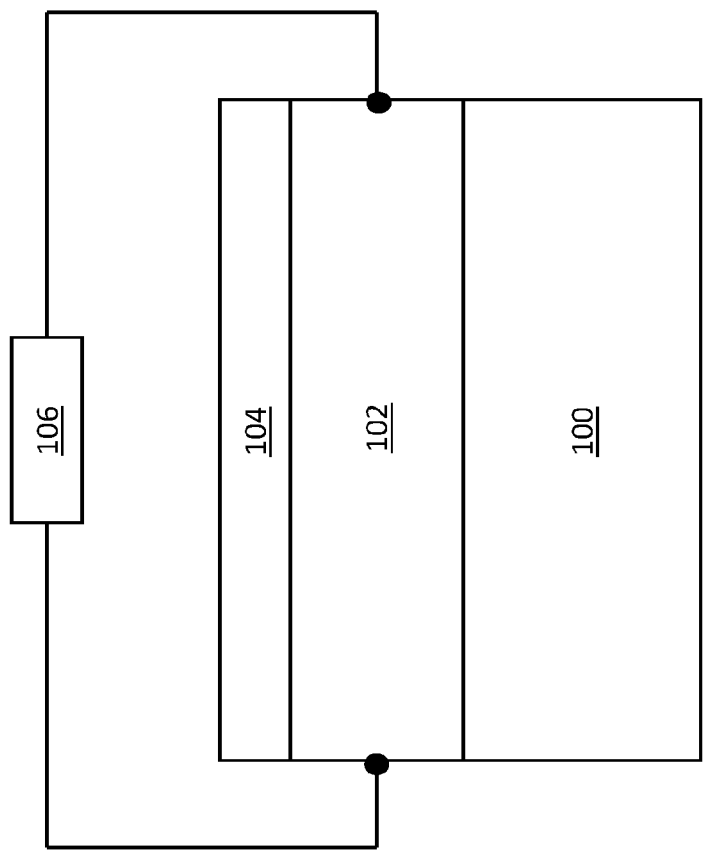
FIG. 1B
FIG. 1A

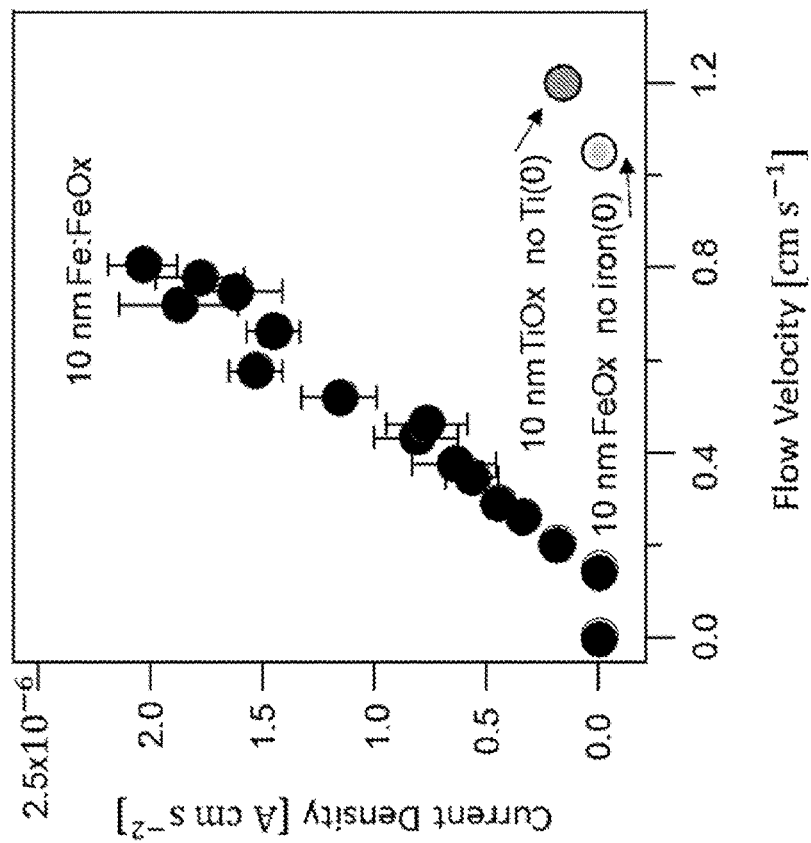
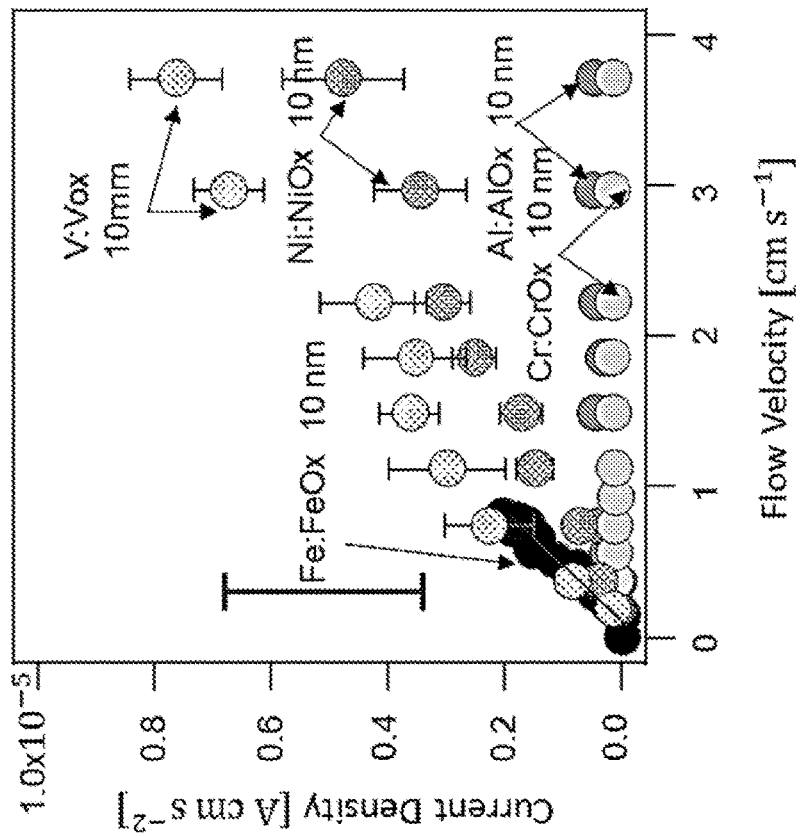
FIG. 9A
FIG. 9B

LIQUID FLOW INDUCED POWER GENERATION USING NANOSCALE METAL LAYERS

CROSS-REFERENCE TO RELATED APPLICATIONS

This application is a National Stage of International Application No. PCT/US19/51421, filed Sep. 17, 2019, which claims the priority benefit of U.S. provisional patent application No. 62/732,822 that was filed Sep. 18, 2018, U.S. provisional patent application No. 62/772,319 that was filed Nov. 28, 2018, and U.S. provisional patent application No. 62/879,923 that was filed Jul. 29, 2019, the entire contents of which are incorporated herein by reference.

REFERENCE TO GOVERNMENT RIGHTS

This invention was made with government support under grant number CHE0950433 awarded by the National Institutes of Health, grant number N00014-10-1-0884 awarded by the NAVY/ONR, and grant number W911NF-19-1-0361 awarded by ARMY/ARO. The government has certain rights in the invention.

BACKGROUND

Current methods and devices for achieving kinetic/gravitational to electrical energy conversion use conducting or semi-conducting layered materials in contact with moving aqueous droplets or brushes. The most successful approaches, based on carbon nanotubes, graphene, and dielectric-semiconductor architectures, are promising as they show efficiencies of around 30 percent. However, even the most successful approaches pose challenges related to fabrication, scaling, and long-term stability during operation in the field.

SUMMARY

Energy harvesting devices and methods of using the devices to convert the mechanical energy of a flowing ionic solution into electric energy are provided. Also provided are flow sensors and methods for using the flow sensors to monitor the flow of an ionic solution, as well as frictionless pumps and methods for using the pumps to move an ionic solution across a surface. The devices utilize the flowing ionic solution to move an electrical double layer across a metal layer, thereby generating a current in the metal layer.

One embodiment of a method of harvesting energy uses a liquid flow-based device that includes: a metal layer comprising a metal; an amphoteric metal oxide film adjacent to the metal layer at an interface, the amphoteric metal oxide film having a surface disposed opposite the interface, wherein the metal layer has a thickness that facilitates charge carrier motion parallel to the interface; and at least one of: an electronic device that consumes electrical power connected laterally across the metal layer and configured to be powered by a current running parallel to the interface; and an energy storage device connected laterally across the metal layer and configured to be charged by a current running parallel to the interface. The method of harvesting energy using said device includes the steps of: exposing the surface of the amphoteric metal oxide film to a flow of an ionic solution having a temporally varying flow rate or a temporally varying flow direction, wherein the temporally varying flow rate or the temporally varying flow direction generates a current in the metal layer; and powering the electronic device or charging the energy storage device with the generated current.

One embodiment of a method of monitoring the flow of an ionic solution uses a liquid flow-based device that includes: a metal layer comprising a metal; an amphoteric metal oxide film adjacent to the metal layer at an interface, the amphoteric metal oxide film having a surface disposed opposite the interface, wherein the metal layer has a thickness that facilitates charge carrier motion parallel to the interface; and at least one of: a voltage measuring device configured to measure a voltage across the metal layer; and a current measuring device connected laterally across the metal layer and configured to measure a current running parallel to the interface. The method of monitoring the flow of the ionic solution includes the steps of: exposing the surface of the amphoteric metal oxide film to a flow of an ionic solution to generate a current in the metal layer, the flow of the ionic solution having a temporally varying ionic conductivity, wherein the temporally varying ionic conductivity is provided by a temporally varying flow rate, a temporally varying flow direction, or both; and measuring changes in the voltage across the metal layer or the current through, the metal layer as the ionic solution passes over the surface of the amphoteric metal oxide film.

One embodiment of a method of pumping an ionic solution uses a liquid flow-based device that includes: a metal layer comprising a metal; an amphoteric metal oxide film adjacent to the metal layer at an interface, the amphoteric metal oxide film having a surface disposed opposite the interface, wherein the metal layer has a thickness that facilitates charge carrier motion parallel to the interface; and a voltage source configured to apply a voltage across the metal layer. The method of pumping the ionic solution includes the steps of: disposing an ionic solution on the surface of the amphoteric metal oxide film; and applying a temporally varying voltage across the metal layer, whereby the temporally varying voltage induces the ionic solution to move along the surface of the amphoteric metal oxide film.

Some embodiments of the liquid flow-based devices that can be used to carry out the above-described, and other, methods include: a metal layer comprising vanadium, copper, or tin; an amphoteric metal oxide film comprising vanadium oxide, copper oxide, or tin oxide adjacent to the metal layer at an interface, the amphoteric metal oxide film having a surface disposed opposite the interface, wherein the metal layer has a thickness that facilitates charge carrier motion parallel to the interface; and at least one of: an electronic device that consumes electrical power connected laterally across the metal layer and configured to be powered by a current running parallel to the interface; an energy storage device connected laterally across the metal layer and configured to be charged by a current running parallel to the interface; a voltage measuring device configured to measure a voltage across the metal layer; and a current measuring device connected laterally across the metal layer and configured to measure a current running parallel to the interface.

BRIEF DESCRIPTION OF THE DRAWINGS

Illustrative embodiments of the invention will hereafter be described with reference to the accompanying drawings, wherein like numerals denote like elements.

FIGS. 1A-1C. FIG. 1A depicts one embodiment of an energy harvesting device. FIG. 1B is a cartoon representation of the use of stacked nanofilms inside a pipe for electrical power extraction from temporally varying ionic solution flows, such as oceanic tides, or flows of alternating salinity in estuaries and fjords. FIG. 1C depicts one embodiment of an energy harvesting device having multiple metal layers and multiple metal oxide overlayers.

FIG. 2A depicts current induced in a 10 nm Fe:FeOx nanolayer (3×1 in$^2$) when flowing deionized (DI) water at pH 5.8 for 20 sec (black segment), followed by 20 sec flow of 1 M NaCl held at pH 7 (grey segment), and six subsequent replicates, all at a constant flow rate of 20 mL min'. FIG. 2B depicts the same as in FIG. 2A but measured using a 3×9 in$^2$ Fe:FeOx nanolayer of 10 nm thickness at a flow rate of 100 mL min$^{-1}$ and 2 min between switching salt concentration. FIG. 2C depicts the same as in FIG. 2B but measured at a flow rate of 35 mL min$^{-1}$ and constant 0.6 M salt concentration while reversing the flow direction every 2 min, marked by the vertical grey lines.

FIG. 4A depicts voltage induced in a 50 nm (black trace) and 10 nm (gray trace) thin iron nanofilm (data offset for clarity); 15 µL drops at a drop rate of 0.5 mL min$^{-1}$. FIG. 4B depicts voltage induced in a 2 mm thick iron plate, commercial aluminum foil (data offset for clarity), and aluminum film inside a snack bag (data offset for clarity); 15 µL drops at a drop rate of 0.5 mL min$^{-1}$.

FIG. 5A depicts open-circuit voltage (OCV) measured perpendicular to the drop motion while dropping a 0.6 M aqueous salt solution (pH 5.8) over a 5 nm thin iron nanofilm at a drop rate=0.5 mL/min and (FIG. 5B) when reversing the polarity of the probes.

FIG. 8A depicts induced current in a 10 nm iron nanofilm using aqueous solutions of alternating salinity (0.1M and DI water, 25 mL min$^{-1}$, 20 sec flow per salinity) over ~1 hour. FIG. 8B depicts induced current before, during, and after low-to-high salinity transition in a flow cell.

FIGS. 9A-9F: Mechanistic Investigations. FIG. 9A depicts average current densities measured as a function of aqueous flow velocity using 10 nm thin nanolayers of Fe:FeOx, Ni:NiOx, V:VOx, Al:AlOx, and Cr:CrOx while alternating DI water (pH=5.8) and 0.6 M NaCl solution (pH~7) segments every 20 sec, and current density obtained for 30 µL drops falling with a 0.1 to 0.2 cm$^2$ contact area onto a 10 nm thick Fe:FeOx nanolayer deposited onto a 1×3 in$^2$ glass substrate while alternating the drop salinity between DI water and 0.6 M at a drop rate of 2 mL min$^{-1}$ and an incident angle of ~160° (vertical bar). Error bars on point estimates shown are for 1 standard deviation (a) from n=7 and 8 replicate measurements per flow rate. FIG. 9B depicts the same as FIG. 9A but for a 10 nm Fe:FeOx nanolayer as a function of aqueous flow velocity and for a 10 nm thin nanolayer of pure FeOx (no metal present) and a 10 nm thin nanolayer of pure TiOx. FIG. 9C depicts current density recorded for Fe:FeOx nanolayers varying in total thickness obtained with a flow velocity of 0.74 cm s$^{-1}$ while alternating DI water and 0.6 M NaCl solution segments every 20 sec. FIG. 9D depicts current density obtained for a 30 nm Fe:FeOx nanolayer without and with a 5 nm Cr:CrOx nanolayer on top of it obtained with a flow velocity of 1.15 cm s$^{-1}$, and for a 30 nm nanolayer of pure FeOx (no metal present) obtained with a flow velocity of 1 cm s$^{-1}$, all while alternating DI water and 0.6 M NaCl solution segments every 20 sec. FIG. 9E depicts current density for Fe:FeOx and Al:AlOx nanolayers as a function of the natural logarithm of the salt concentration difference in solutions of alternating salinity recorded using 30 µL drops at a drop rate of 2 mL min$^{-1}$ (flow velocity=0.3 cm s$^{-1}$, assuming a 0.1 cm$^2$ contact area of the rolling drop). Error bars on point estimates shown are for 1 standard deviation (σ) from n=O (100) replicate measurements. FIG. 9F depicts the natural logarithm of the current density (in A cm$^{-2}$) as a function of change in Gouy-Chapman surface potential (σ=0.007 C m$^{-2}$) resulting from changing the ionic strength when altering the salt concentration.

FIG. 14A depicts atom probe tomography reconstruction of the heterostructured Fe:FeOx nanolayer (center). Iron oxide and iron metal shown separately on top and bottom, respectively. FIG. 14B depicts an all-atom representation of the heterostructured nanolayer, including the metal conductor (gray) and a nonpolarizable oxide overlayer and with columnar subsurface heterostructure (darker outlined circles); a single probe Na+ cation is shown at a distance of 1.6 angstroms from the nanolayer. FIG. 14C depicts induced charge distribution, Q (x), by the Na$^+$ cation at four different lateral positions relative to the position of the nonpolarizable heterostructure. FIG. 14D depicts ion-nanolayer Coulomb interaction as a function of lateral ion position, for various widths, d, of the nonpolarizable heterostructure; $4E^{coul}$ is the difference in the ion-nanolayer Coulomb interaction for the nanolayer systems with and without the subsurface heterostructure. FIG. 14E depicts a molecular dynamics (MD)

simulation snapshot for alternating regions of ionized (0.43 M NaCl) water/DI water in contact with the nanolayer with columnar heterostructure (d=1.3 nm). The nanolayer is shown as in FIG. 14B, but with the instantaneous charge polarization of metal conductor atoms also indicated (range=[−0.005 e (black), +0.005 e (dark grey)]). Vertical dotted lines indicate semipermeable boundaries for the ions to preserve the salinity boundaries. FIG. 14F shows, for the simulation cell shown in FIG. 14E, the time-averaged induced charge distribution, Q (x), as well as the 0.5-ns block averages of the same quantity. FIG. 14G shows a comparison of the time-averaged induced charge distribution for the system with and without nonpolarizable heterostructure.

DETAILED DESCRIPTION

Figure 1C:
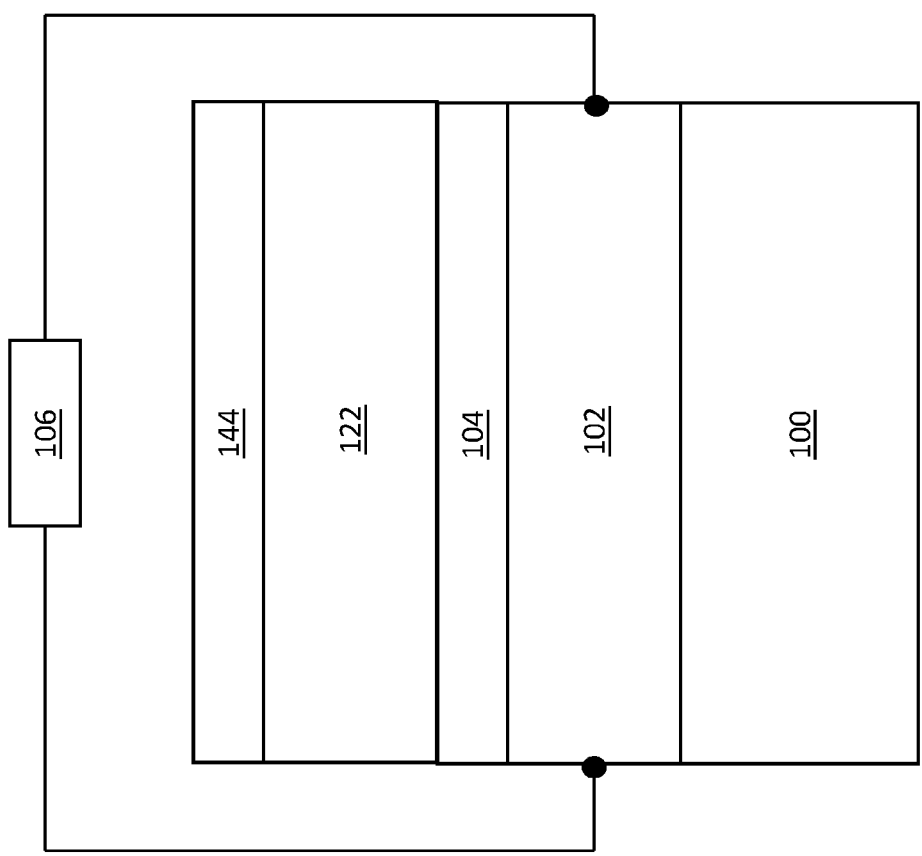

Energy harvesting devices and methods for converting the mechanical energy of a flowing ionic solution, such as rainwater or seawater, into electric energy are provided. Also provided are flow sensors and methods for using the flow sensors to monitor the flow of an ionic solution, as well as friction less pumps and methods for using the pumps to move an ionic solution across a surface.

One embodiment of an energy harvesting device (FIG. 1A) includes an electric current generating device that includes a metal substrate composed of at least one metal layer 102 and an amphoteric metal oxide film 104 disposed over a surface of the metal layer. The metal layer, which may be disposed on a support 100, acts as an electrical conductor and, in some embodiments, has a thickness that is no more than an order of magnitude greater than the length of the mean free path of an electron in the metal of the metal layer. The energy harvesting device further includes an electronic device 106 that is powered by the electric current generating device or an energy storage device that is charged by the electric current generating device. Electronic device 106 can be any electrical component that consumes electrical power, such as a light, a computer, or an appliance. In contrast an energy storage device is one that stores electrical power, such as a battery or a capacitor.

Although the inventors do not intend to be bound to any particular theory of the invention, the operation of the device can be considered as follows. When an ionic solution (that is—a solution that contains ions) passes over the amphoteric metal oxide film, an interface is formed between the ionic solution and the amphoteric metal oxide. This interface is characterized by a distribution of anions, cations, and water molecules within electrical double and diffuse layers, which are collectively referred to as the EDL, and the protonation state of the surface hydroxyl groups terminating the oxide. If the amphoteric oxide film is thin enough, the electrostatic potential can reach through the film and polarize the underlying metal. As a result, it is possible to generate an electric current in the conductor beneath the metal oxide overlayer by moving an electrical double layer across it, particularly if the space available for charge mobility in the metal layer is horizontally confined and comparable to the electron mean free path in the conductor. The directional electron flow can be confined by limiting the thickness of the metal layer to the nanoscale using, for example, a dendritic amphoteric metal oxide or other overlayer of lesser electrical conductivity than the conductor on one side of the conductor (for example, the top side), and an insulating support on the opposing side (for example, the bottom side). The directional electron flow can also be confined by limiting the thickness of the metal layer to the nanoscale by using a dendritic amphoteric metal oxide or other overlayer of lesser conductivity on both sides (top and bottom) of the conducting metal layer.

The metal layer can be formed on the support in a single step using a physical or chemical vapor deposition process, such as electron-beam physical vapor deposition (PVD). Electron-beam PVD methods for making high purity metal layers, including iron layers, are described in U.S. Pat. No. 9,738,966. An amphoteric oxide overlayer can form spontaneously on the surface of the metal layer in an oxygen-containing environment, such as ambient air. The metal layer should be grown to a thickness that is comparable to the mean free path of the electrons in the metal from which it is made; this imparts hardness to the layer and facilitates charge motion parallel to the metal layer/metal oxide film interface, as opposed to away from (i.e., perpendicular to) said interface. The metal can be of very high purity so that the growth of the oxide overlayer self-terminates before it reaches a thickness of more than several nm. For example, the metal oxide layer may grow to a thickness in the range from 0.5 to 10 nm. Such self-terminating oxidation results in a structure that is stable over long periods. The thickness of the metal oxide film can be controlled based on the metal used in the metal layer, the thickness of the underlying metal layer, and the purity of the metal. By way of illustration, the metal layer will typically have a thickness of no greater than, or on the order of, 500 nm and the metal oxide overlayer (also referred to as the metal oxide film) will typically have a thickness of no greater than, or on the order of, 10 nm. This includes embodiments in which the metal layer has a thickness of no greater than 100 nm and further includes embodiments in which the metal layer has a thickness of no greater than 50 nm, and the metal oxide overlayer has a thickness of no greater than 8 nm. By way of illustration, in some embodiments, the metal layer has a thickness in the range from 8 nm to 100 nm, and the metal oxide film has a thickness in the range from about 2 nm to 7 nm.

In some embodiments, the device includes a multilayered film that includes multiple (i.e., two or more) metal layers with the same composition or with different compositions in a stacked configuration. Optionally, each of the metal layers can be oxidized prior to the deposition of the next metal layer to provide a stack of alternating metal layers and metal oxide films. In embodiments where the metal layers in the stack have different compositions, the metal layers and their corresponding metal oxide films can comprise metal alloys or mixtures of different metal elements formed by the co-deposition of the metals. One embodiment of a device that includes a multilayered film is shown in FIG. 1C, where components common to the device of FIG. 1A and FIG. 1C as designated with like numbers. By way of illustration, the metal layers can include an iron layer, followed by a chromium layer, followed by an aluminum layer or the metal layers can include a first iron layer 102, followed by a second iron layer 122, wherein each metal layer has a corresponding metal oxide overlayer, 104, 144.

In some embodiments of the devices, the metal layer is a high purity, zero-valent iron layer. However, other metals that form thin, self-passivating amphoteric oxides can also be used, wherein an amphoteric oxide is an oxide that can act both as an acid and as a base according to Brønsted-Lowry Theory. These metals include, but are not limited to, aluminum, zinc, copper, tin, chromium, nickel, and vanadium. The amphoterism of the oxide overlayer can be used to determine the sign and magnitude of the charge and potential distributions within an EDL under conditions of varying aqueous pH and ionic strengths. Specifically, the point of zero charge (PZC) of the oxide overlayer may be above or below the pH of the ionic solution, determining whether the surface charge density is positive or negative, respectively. The further away from the PZC the pH is, the larger the magnitude of the oxide overlayer surface charge density. Likewise, for a given oxide overlayer surface charge density, the ionic strength in the ionic solution above the oxide overlayer determines the magnitude of the electrostatic potential emanating from it.

The use of high purity zero-valent iron nanofilms may be advantageous because large area films can be formed using PVD techniques using relatively inexpensive and commercially available standard purity starting materials, as demonstrated in Example 1. In addition, the optical properties of the amphoteric iron oxide overlayers also enable the generation of charge carriers via exposure to visible light. The use of metals having biocidic properties, such as aluminum, zinc, and silver, can be beneficial for protecting against biofilm formation for applications where such formation is undesirable.

In some embodiments of the devices, the metal of the metal layer forms dendrites, which are finger-like structures. These dendrites can be used to facilitate the directional flow of electrons in the layer. Dendrites can be formed when the metal oxidizes in air once vapor deposition is complete. By controlling the oxygen partial pressure, relative humidity, and temperature, the structure, number density, width and depth of the metal oxide dendrites can be adjusted to optimize charge mobility along the potential hotspots on the dendrites and minimize possible leakage due to tunneling.

Metals that form redox-active oxides, that is—oxides that contain the metal in more than one oxidation state, generally produce higher currents. Therefore, embedding metal atoms having multiple charge states, such as chromium and/or iron, in the metal layer can increase the current produced by the devices described herein. In addition, current generated can be increased by increasing the carrier density in the metal oxide overlayer. Therefore, the metal oxide overlayer can be chemically doped with either n-type or p-type extrinsic dopants in order to increase current generation. Such dopants include those commonly employed in semiconductor doping. Embedded atoms and dopants can be introduced into the metals and metal oxides using, for example, chemical vapor deposition. By way of illustration, suitable dopant concentrations include those in the range from $10^{13}$ $cm^{-3}$ to $10^{13}$ $cm^{-3}$. However, concentrations outside of this range can be employed.

The support upon which the metal film is formed can be electrically insulating. Examples of materials from which the support can be made include glass, marble, and organic polymers, such as polypropylene or polyethylene. The supports may be rigid or mechanically flexible.

The electric current generating devices operate by exposing a surface of the amphoteric metal oxide film facing opposite the metal layer/metal oxide film interface to a flow of ionic solution that imparts a varying surface potential on the metal oxide film. The flow rate can vary over a broad range. For example, in some embodiments of the methods for harvesting energy, ionic solution flow rates of at least 0.5 mL/min, at least 10 mL/min, and at least 20 mL/min. However, lower flow rates can also be used. The concentration of ions in the ionic solution can be, but need not be, quite low. By way of illustration, the ion concentration level of the flowing liquids used to operate the devices described herein may be in the range from about 0.1 mM to 2 M, including in the range from 0.1 M to 1 M. The flow of ionic solution can be generated by natural phenomena or by non-naturally occurring mechanical means, such as by pumps, including used for urban discharge management or desalination.

The movement of an EDL across the surface of the metal oxide film can be achieved in several ways. First, intermittent flow of the ionic solution can be passed over the surface. A flow of discrete, separated droplets is an example of an intermittent flow stream. Waves periodically flowing over the device surface are another example of an intermittent flow stream.

However, the ionic solution need not be intermittent. For example, the device can be operated using a flow of ionic solution having a temporal variation in ionic conductivity. A temporal variance in the ionic conductivity can be achieved by using a continuous flow of a liquid stream having a substantially constant flow rate and direction, but a non-uniform ion concentration within the stream along the direction of the flow. An intermittent flow may be a flow of water having a given salinity alternating with air or similarly sparingly miscible matter to sharpen the screening potential gradient along the metal oxide overlayer. This can be achieved by a liquid stream having alternating sections (e.g., plugs) of a first ionic solution having a first ionic conductivity and second sections (e.g., plugs) of a second liquid, which may also be an ionic solution, having a lower conductivity than the first ionic solution. The sections of the second liquid in a continuous liquid stream can be formed from a liquid that is immiscible with the first ionic solution. By way of illustration, a liquid stream comprising aqueous sections interspersed with oil sections in a tube, such as a capillary tube, could be used. Natural bodies of water can also create a liquid flow with a temporally varying ionic conductivity (e.g., temporally varying salinity) to move a screening potential along the metal oxide overlayer to generate a current in the underlying metal layer. For example, the salinity levels in some natural bodies of water, such as some marine environments, estuaries, and fjords, vary with the tidal cycle. Therefore, a water flow generated by the tidal cycle of such bodies of water could be used to provide a liquid flow with a temporally alternating salinity.

The movement of an EDL across the surface of the metal oxide film can also be achieved by using a flowing ionic solution that has a temporally varying flow rate and/or a temporally varying flow direction. A temporally varying flow rate can be achieved by modulating the velocity of an ionic solution stream as it flows over the surface of the device. For example, the flow rate of the ionic solution can be modulated from a first (higher) flow rate to a second (lower) flow rate and then to higher flow rate again in repeated cycles; that is—the ionic solution can undergo cyclic fast-slow flow. Instead of, or in addition to, the flow rate, the direction of flow can also be modulated to create a flow with an oscillating direction over the device surface. For example, the direction of the ionic solution flow can be changed from a first direction (e.g., forward flow) to a second direction (e.g., backward flow) in repeated cycles to induce a varying potential in the metal layer of the device. For embodiments of the methods that rely on a varying flow rate and/or a varying flow direction, the ionic concentration of the flowing solution can remain constant throughout the flow process.

One application for devices that use ionic solutions with temporally varying flow rates is as blood flow sensors or as blood flood energy harvesting devices, since blood is an ionic solution that is naturally pumped with a temporally varying flow rate. Thus, the devices described herein can be used in vitro or implanted in vivo in a vein or artery such that blood flowing over the amphoteric metal oxide film generates a current in the metal substrate. The resulting current can be use as the basis for a blood flow rate sensor or as the basis for an energy harvesting device.

It should be noted that the use of varying flow rates, varying flow directions, and varying ion concentrations are not mutually exclusive. In some embodiments of the devices, one or more of the flow rate, the flow direction, and the ion concentration of the ionic solution flow may change as the flow passes over the amphoteric metal oxide of the devices.

The ionic solution can be a solution containing solvated ions and having a sufficiently high ion concentration to generate an electric current. For example, an aqueous salt solution, including rainwater or salinized water or brine from a natural body of water, such as a sea or a river, with an ionic strength as low as 0.1 mM, can be utilized. Other sources for an ionic solution include waste brine from a water desalination facility, wastewater from a wastewater treatment plant, urban water discharge, ground water, and glacier water. However, other ionic solutions, including liquid containing salts other than sodium chloride can be used. For example, other ionic salts, including other halide salts can be used. Such salts include both monovalent salts and multivalent salts, such as $YCl_3$, as illustrated in Example 2 and Example 3.

As discussed above, some embodiments of the devices utilize a flow of droplets, including, for example, raindrops, for flow induced power generation. In embodiments of these devices, a flow of the liquid droplets falls onto the surface of the amphoteric metal oxide film and slides down the surface under the force of gravity. As the droplets pass over the surface, they generate a unidirectional electron current in the metal layer by moving a screening potential along the metal oxide film. Raindrop-induced power generation can be implemented by using a window for a building as the support for fabricating the current generating device. Because the metal layers and their metal oxide films can be made optically transparent to visible and solar radiation, they can be formed using a window for a building as a support. Since the ionic strength of rainwater (~0.2 mM) is sufficiently high to polarize the interface, the resulting window could be used to harvest power from the raindrops and/or act as a rain sensor. Other ionic solution sources that could be used to provide a discontinuous flow of an ionic solution include waves and tides.

As illustrated in FIG. 1B, stacks or rows of the current generating devices 110 can be built into a pipe 112 or channels, and wave action, propulsion, ocean currents, or tidal movements due to gravitational forces from outside the earth can be used to generate a flow of salt-containing water through or over the electric current generating devices. This approach can satisfy an operational requirement of having to move a dynamically changing electrical double layer structure across the metal oxide film, and do so over long distances. By coupling (e.g., connecting in parallel or series) a plurality of the current generating devices, substantial power generation can be achieved.

The current generated in the metal layers of the current generating devices can be harnessed by connecting an electrical device, such as a household appliance, or an electrical energy storage device, such as a capacitor or battery, laterally across the metal layer. For the purposes of this disclosure, an electrical device or a storage device can be considered connected "laterally" across the metal layer as long as it is connected in such a configuration that the directional current generated in the metal layer and moving parallel to (as opposed to perpendicular to) the metal/metal oxide interface provides power for the electronic device or charges the storage device. The connection may include additional active or passive electronic components, and the electrical device or the storage device can be connected across more than one current generating device. As shown in FIG. 1A and FIG. 1C, a laterally connection across the metal layer can be a connection from one edge of the metal layer to the opposing edge.

The current generating devices can also be used as flow sensors. One basic embodiment of a flow sensor includes a current generating device, as described herein, and a voltage measuring device, such as an oscilloscope, or current measuring device connected laterally across the metal layer of the current generating device in a configuration whereby the voltage or current measuring device measures the voltage across, or current through, the device as a flow of an ionic solution passes over the surface of the amphoteric metal oxide film. The general structure of a flow sensor is shown in FIG. 1A and FIG. 1C, where reference number 106 represents a voltage measuring device or current measuring device, rather than an electronic device. (The relative thicknesses of the layers in FIGS. 1A and 1C are not to scale.)

The devices also can be run in "reverse", whereby droplets of an ionic solution can be moved across the surface of the amphoteric metal oxide film by, for example, putting in non-Faradaic currents or applying a voltage across an ionic solution disposed on the amphoteric metal oxide. As such, the devices can operate as a silent and frictionless pump without any moving parts to move ionic solutions against the force of gravity, as illustrated in Example 4.

EXAMPLES

Example 1. This example reports kinetic:electrical energy transduction using nanolayers formed in a single step from earth-abundant elements. The method utilizes large-area PVD onto rigid or flexible substrates that can be readily scaled to arbitrarily large areas. In addition to flowing aqueous droplets across the nanolayers, current is shown to be created either with linear flow of salinity gradients or with oscillatory flow of a constant salinity. The operational principle of moving a dynamically changing electrical double layer (a "gate") across the nanostructure identified in prior approaches is confirmed for the new structures and augmented by occurrence of electron transfer within the thermal oxide nano-overlayers terminating the metals. The simplicity of the approach allows for rapid implementation. This example illustrates the formation of single- and dual-element nanolayers from low-cost 99.95% purity iron, 99.98% Ni, 99.7% V, 99.9995% aluminum, and 99.994% chromium sources. XPS reveals a lack of common low-boiling point contaminants like calcium, magnesium, sodium, or zinc in the iron nanolayers and shows the presence of an ~3 nm thin oxidized iron nano-overlayer. Grazing incidence angle X-ray diffraction (XRD) experiments indicate the presence of crystalline $Fe^0$ with low index faces exposed but no crystallinity of the iron oxide overlayer. Control experiments show that this nano-overlayer forms spontaneously when the iron nanolayer is exposed to air and remains stable over prolonged (years) periods of time. Raman and XPS spectroscopy of the iron nanolayers indicate that the oxide nano-overlayer is composed of some Fe (III), $Fe_3O_4$, and other forms of iron oxide. Given the nm-scale spatial variation of the oxide nano-overlayer thickness revealed by the atom probe tomography (APT) experiments, corresponding heterogeneities are expected in the electrostatic potentials—and charge distributions—in the metal below as well.

Fe:FeOx nanolayers having 5, 10, 20, and 50 nm thickness were prepared, which differed in their transparency. 5 and 20 nm thin Al:AlOx and 10 nm Cr:CrOx, V:VOx, and Ni:NiOx nanolayers were also prepared. Nanolayers were deposited onto 3×1 in$^2$ as well as 3×9 inch glass microscope slides. The small slides were placed into a small Teflon cell containing a flow channel (6 mm×7.5 mm×35 mm) Viton-sealed to the metal nanolayers. The large slides were covered with a 1 mm thick silicone sheet into which a 180 mm×15.2 mm wide opening was cut that was then covered by a 1×3×8 in$^3$ Kalrez block containing an in- and outlet fitting (NPT) to connect to a dual pump flow system and waste. After layering a second silicone sheet and a plexiglass cover on top, this large cell was sealed using large-area mechanical clamps.

Aqueous solutions consisted of DI water containing varying amounts of NaCl, equilibrated with ambient air, thus reaching a pH of 5.8. For higher salt concentrations up to 2 M, the pH was adjusted to 8, given the relevance to ocean water and brine. "Instant Ocean" was used as well. Second harmonic generation $\chi^{(3)}$ measurements of the iron nanolayer indicated a negative interfacial charge density of $-0.007$ (3) C m$^{-2}$ at pH 7, consistent with a considerable number density of deprotonated Fe—OH groups at the oxide/water interface near neutral pH. The change in interfacial electrostatic potential, $\Phi$ (0), or "gate" voltage, estimated from Gouy-Chapman theory, would then be in the $-100$ mV range when changing the salt concentration from 0.1 mM to 1 M.

Figure 2A:
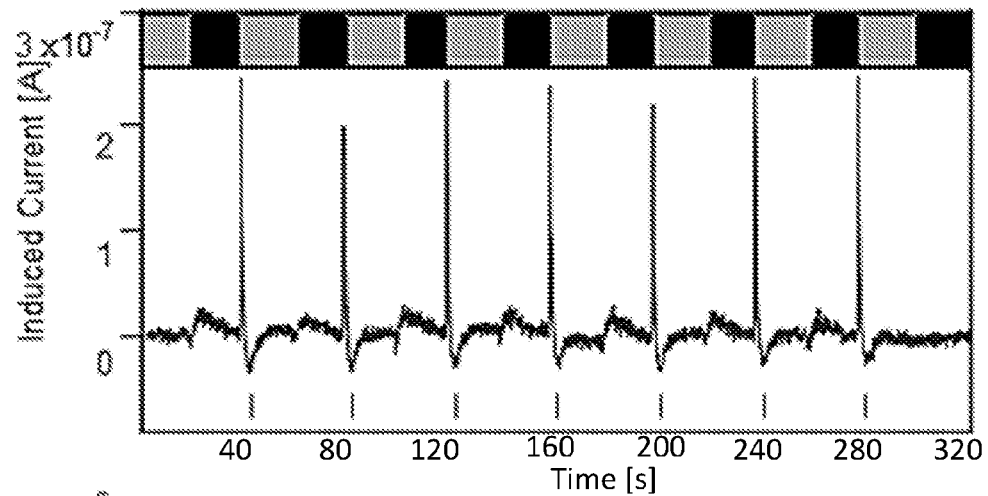
FIGS. 2A-2C: Current and Voltage Measurements.
Figure 2B:
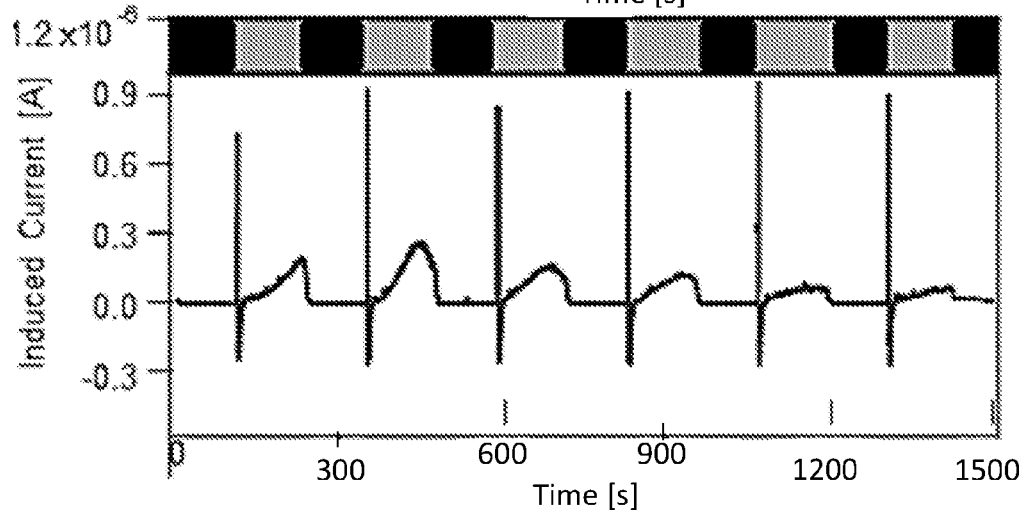
Figure 2C:
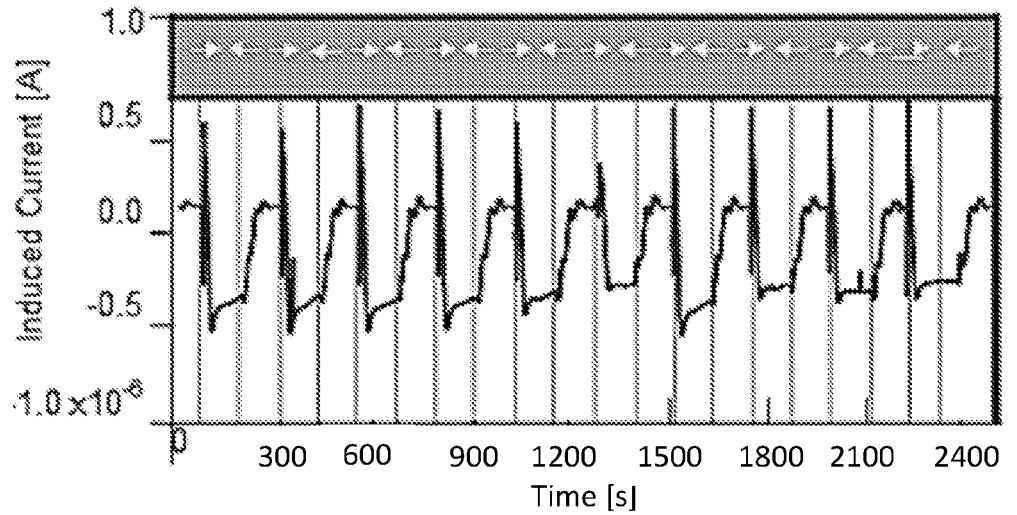
Figure 3:
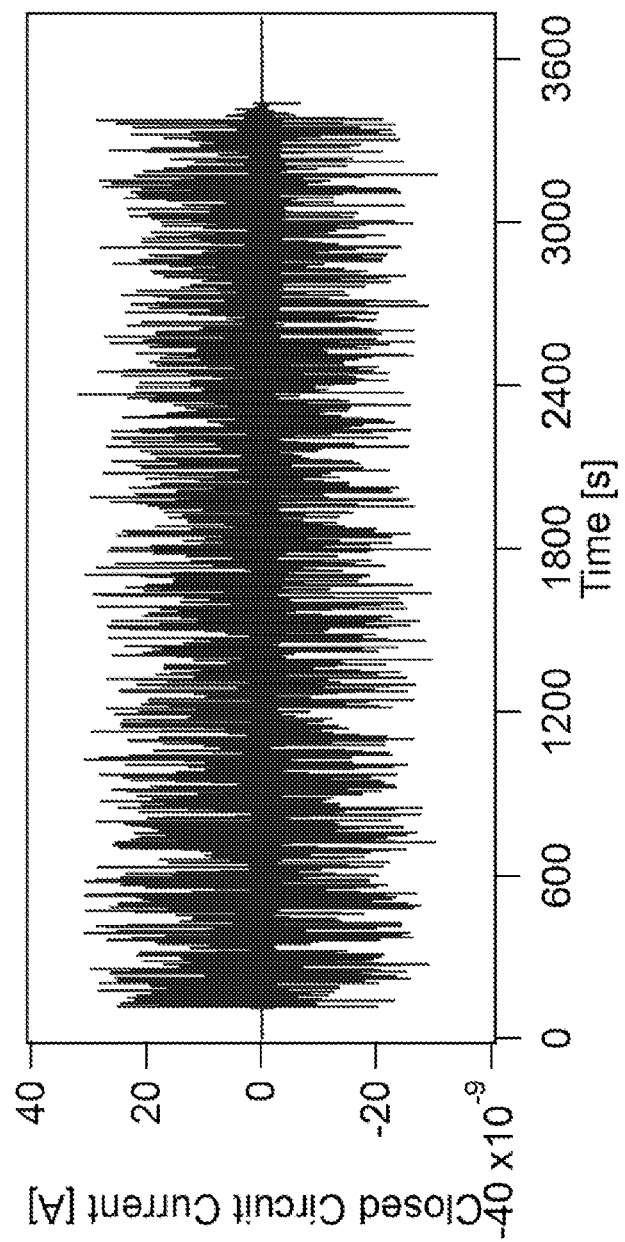
FIG. 3 depicts closed circuit current for a 10 nm thin iron nanolayer under flow of 600 mM NaCl at pH 8.0 lasting 2 seconds alternating with air flow lasting 2 seconds at a flow rate of 28 mL min$^{-1}$.

When flowing water of alternating salinity at 20 mL min$^{-1}$ across a ~10 nm thin Fe:FeOx nanolayer in the small cell, currents of ~0.2 μA (FIG. 2A) and voltages in the mV range were recorded. Currents approaching 1 μA were obtained in the large cell (FIG. 2B, note that the ionic strength gradient in the large cell was about ten times larger than that of the small cell, vide infra). When periodically alternating the direction of aqueous flow at constant ionic strength and constant flow rate in the large cell, current was generated as well (FIG. 2C), albeit in an asymmetric 1 vs. t pattern attributed to the differences in inlet vs. outlet size in the flow cell used. Current was also generated when alternating aqueous solutions of 600 mM NaCl with air (FIG. 3), albeit at a smaller magnitude compared to continuous aqueous flow.

Figures 4A, 4B:
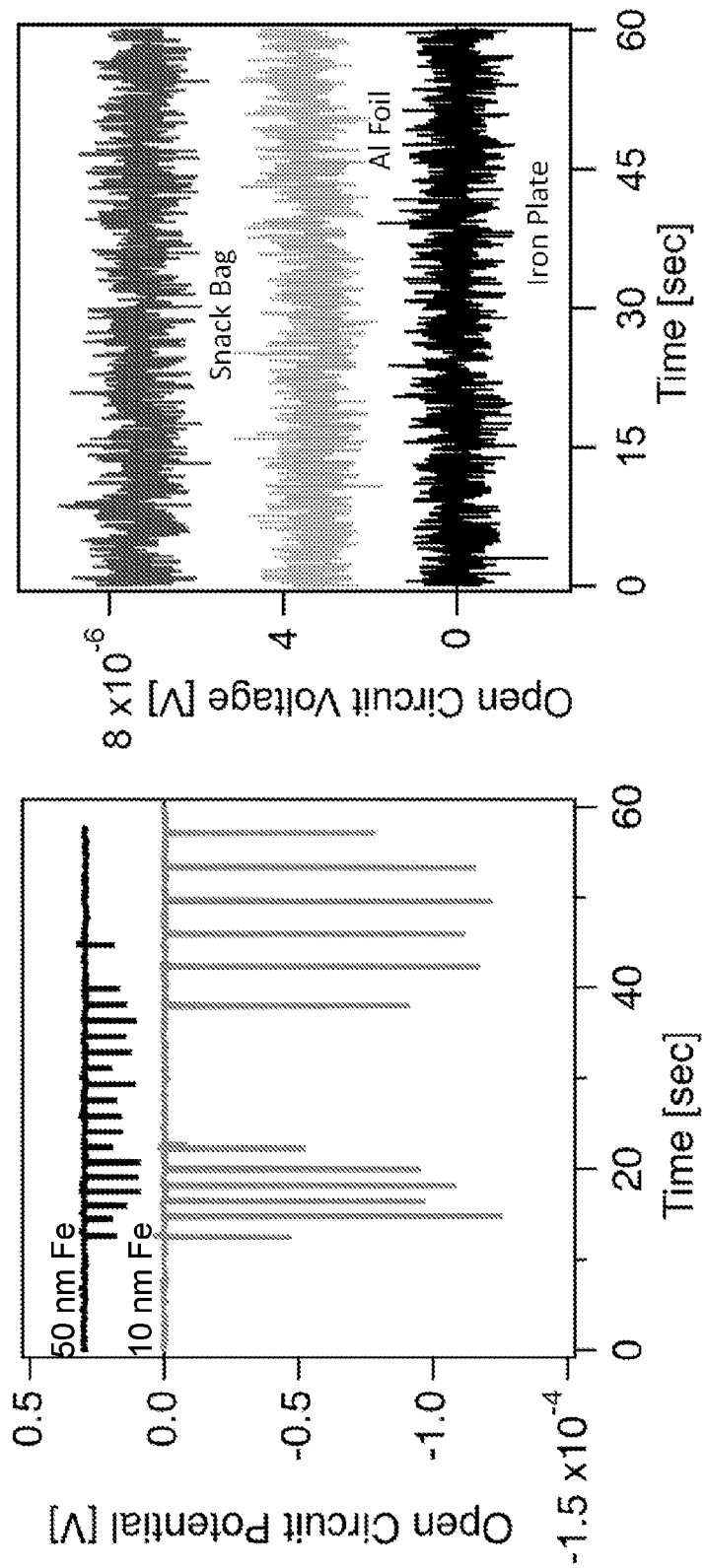
FIGS. 4A-4B.
Figures 5A, 5B:
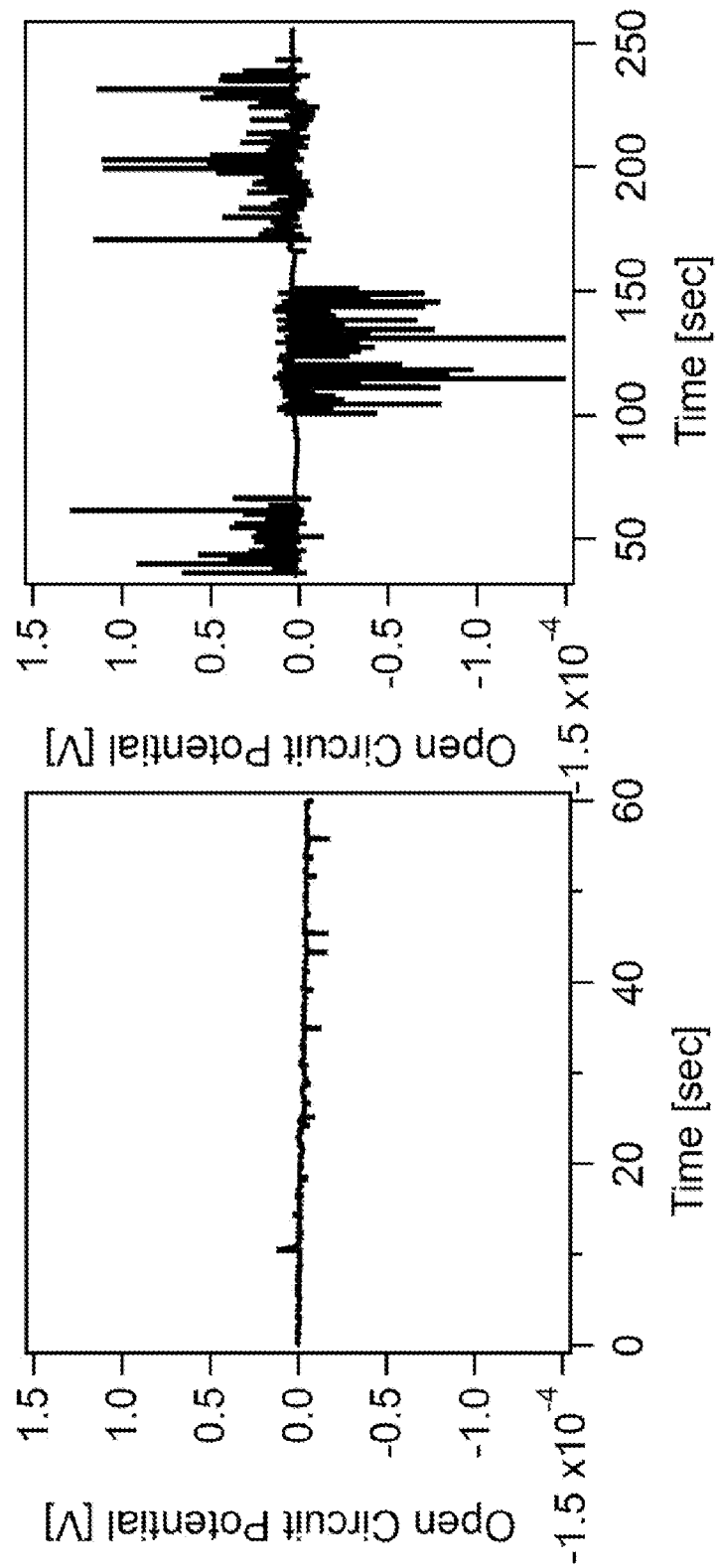
FIGS. 5A-5B.
Figure 6:
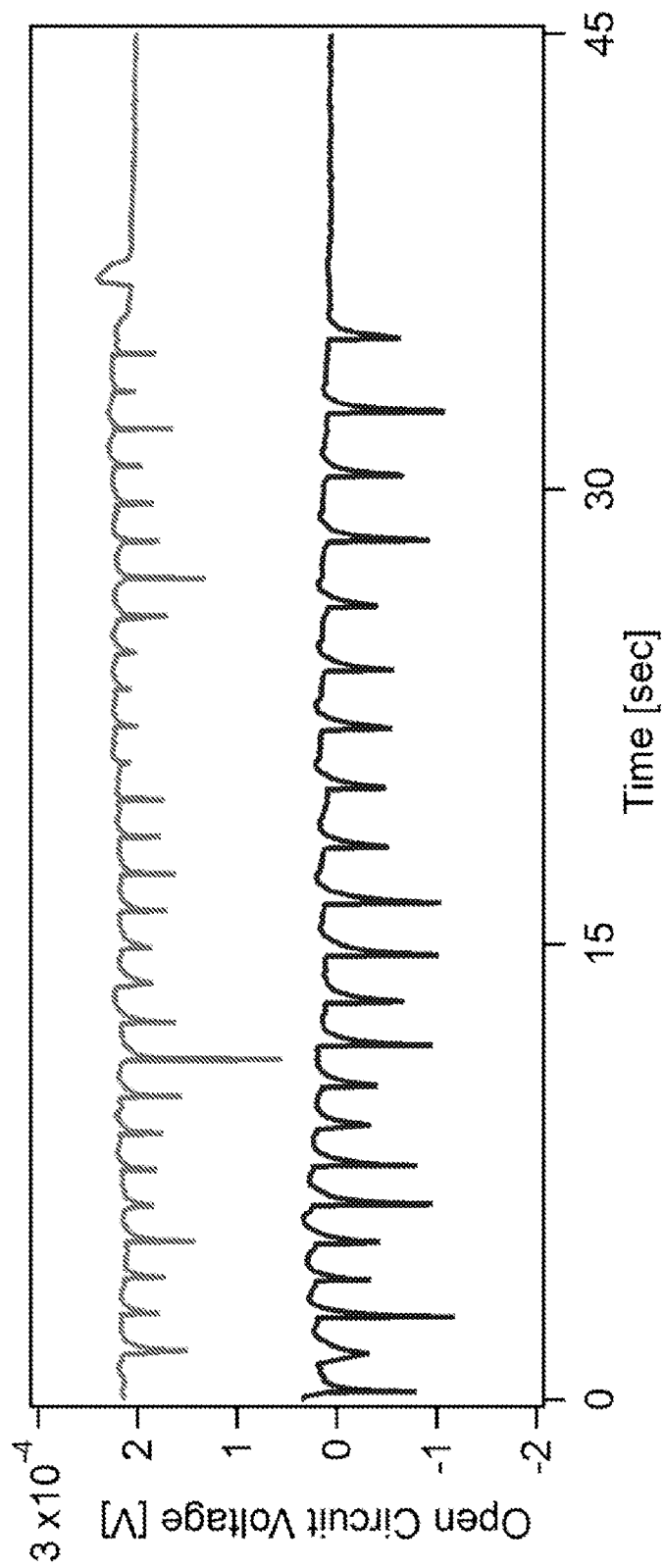
FIG. 6 depicts OCV for a 10 nm thick iron nanofilm using 600 mM salt (top, pH 5.8, offset by 0.2 mV for clarity) and Instant Ocean (bottom, pH 8.3) (drop rate=0.5 mL min$^{-1}$).
Figure 7:
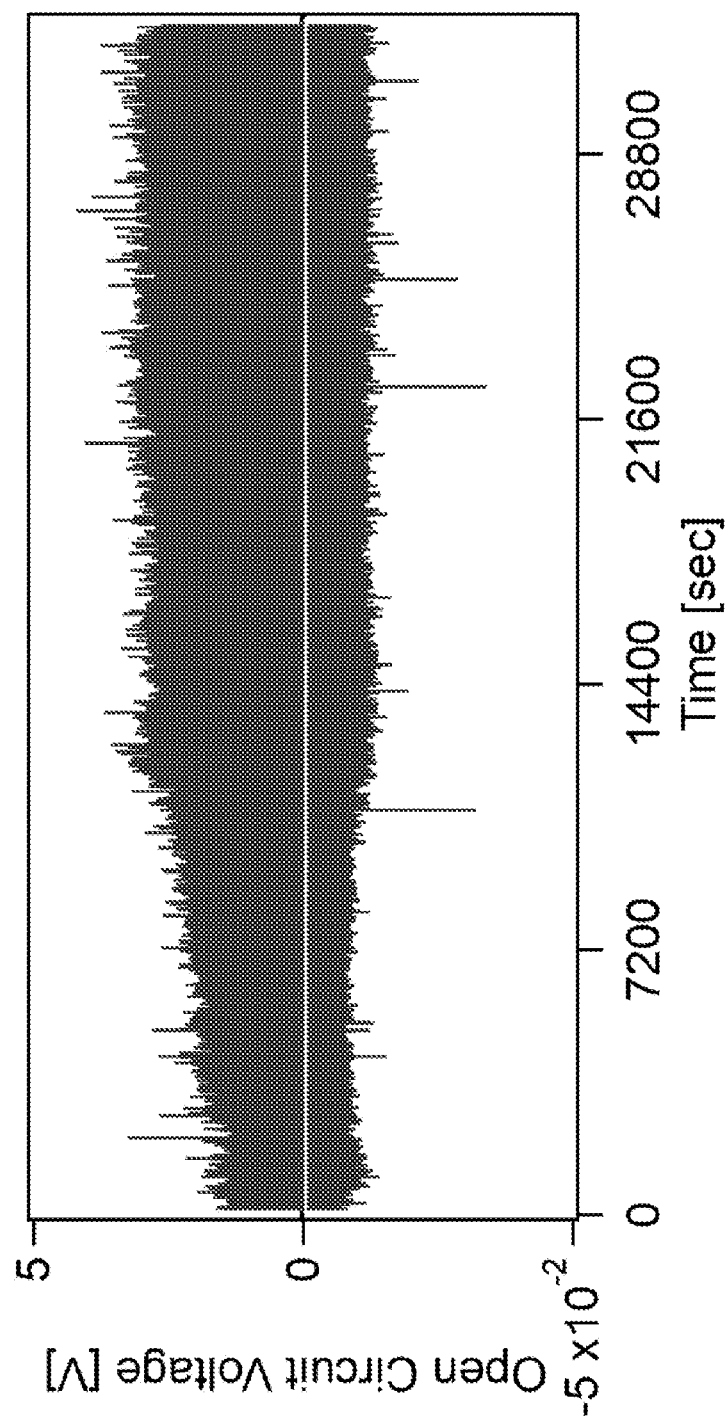
FIG. 7 depicts OCV for a 10 nm thick iron nanofilm using drops alternating between 0.2 mM NaCl at pH 5.8 and 600 mM NaCl at pH 8.0 with a drop rate of 0.5 mL min$^{-1}$.
Figure 8A:
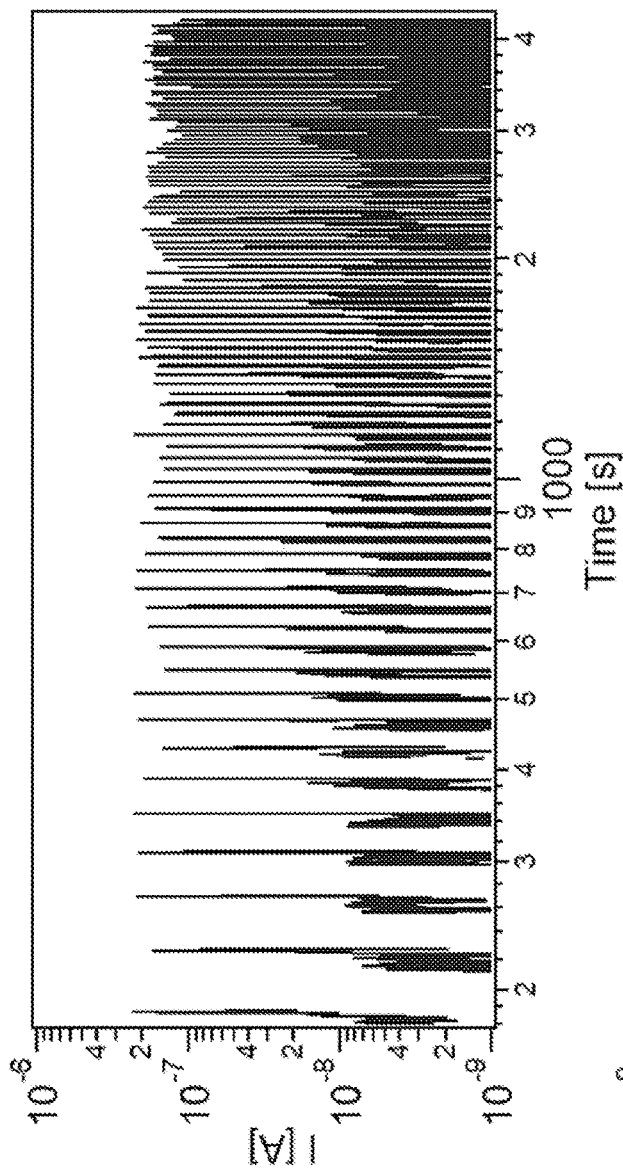
FIGS. 8A-8B.
Figure 8B:
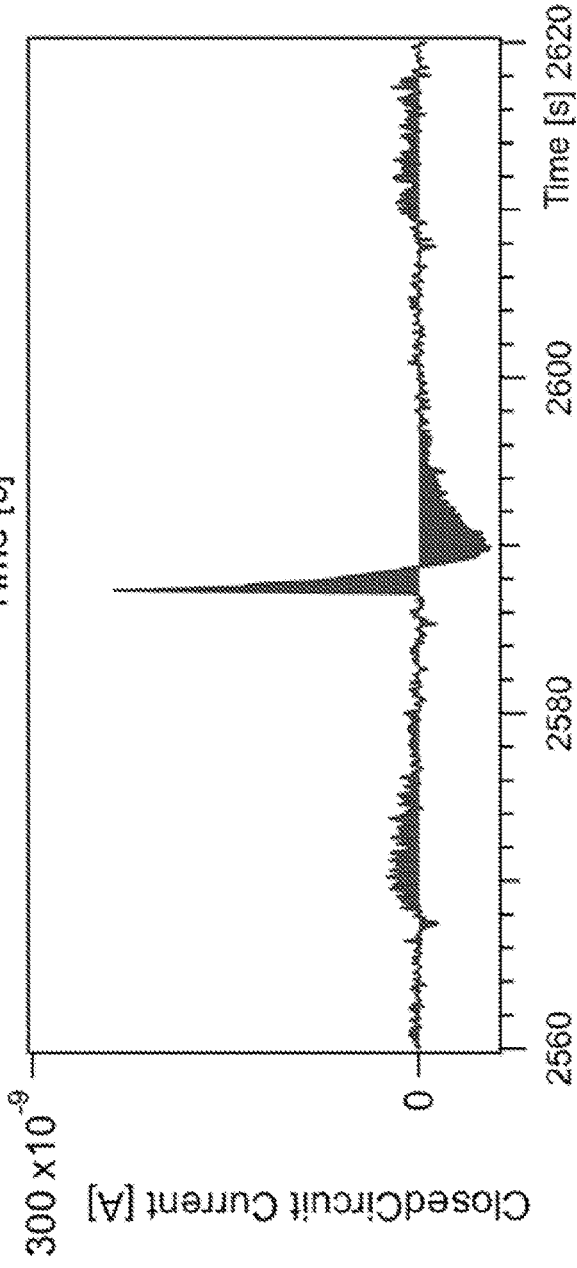

Controls using open circuit voltage measurements show that increasing the iron layer thickness to 50 nm (measured via ellipsometry) leads to considerably smaller open circuit potentials when compared to thinner layers (FIG. 4A), while commercially available aluminum foil, aluminized polypropylene constituting a snack bag wrapping (~100 nm metal layer), a 2 mm thick sheet of iron metal (Alfar Aesar, 99.995%), or aluminum containing its native (thermal) oxide layer show no induced voltage (FIG. 4B). When using drops as opposed to continuous aqueous flow, it was found that measuring the potential across as opposed to along the direction of drop motion shows little voltage during drop motion (FIG. 5A), and that reversing the polarity of the probes reverses the sign of the measured open circuit potential (FIG. 5B). 0.6 M salt solutions representing the salinity of ocean water induce larger voltages than 0.1 M salt solutions that are comparable to those when using "Instant Ocean" (FIG. 6). Alternating the drop salinity between that of the ocean (0.6 M, pH 8) and rainwater (0.2 mM, pH 5.8) induces regular current spikes over >8 hours (FIG. 7). Using the small flow cell, the dynamics of the current flow can be correlated with the flow dynamics inside the flow cell (FIGS. 8A and 8B) for further improvement. Still frames from video recordings using clear and purple-colored water sources reveal a sharp concentration gradient in the flow cell during the time of maximum current generation, from which the "gate" footprint is conservatively estimated to be 7.5 mm channel width×2 mm gradient width for subsequent estimations of current density, j, in the small cell. A similar analysis of the gradient in the big cell shows its footprint is ~2 cm. Alternating the salinity in drop experiments (FIGS. 8A and 8B) produces several tens of mV in open circuit potential that are stable for hours. Additional experiments show induced currents and voltages with an external load resistance of up to 0.5 megaohm placed in series with the nanolayer. Of over 100 metal nanofilms prepared for this Example, each produced comparable current (within a factor of 2) for comparable conditions of nanolayer thickness, flow cell dimensions, flow velocity, aqueous phase composition, and metal type.

Figure 10:
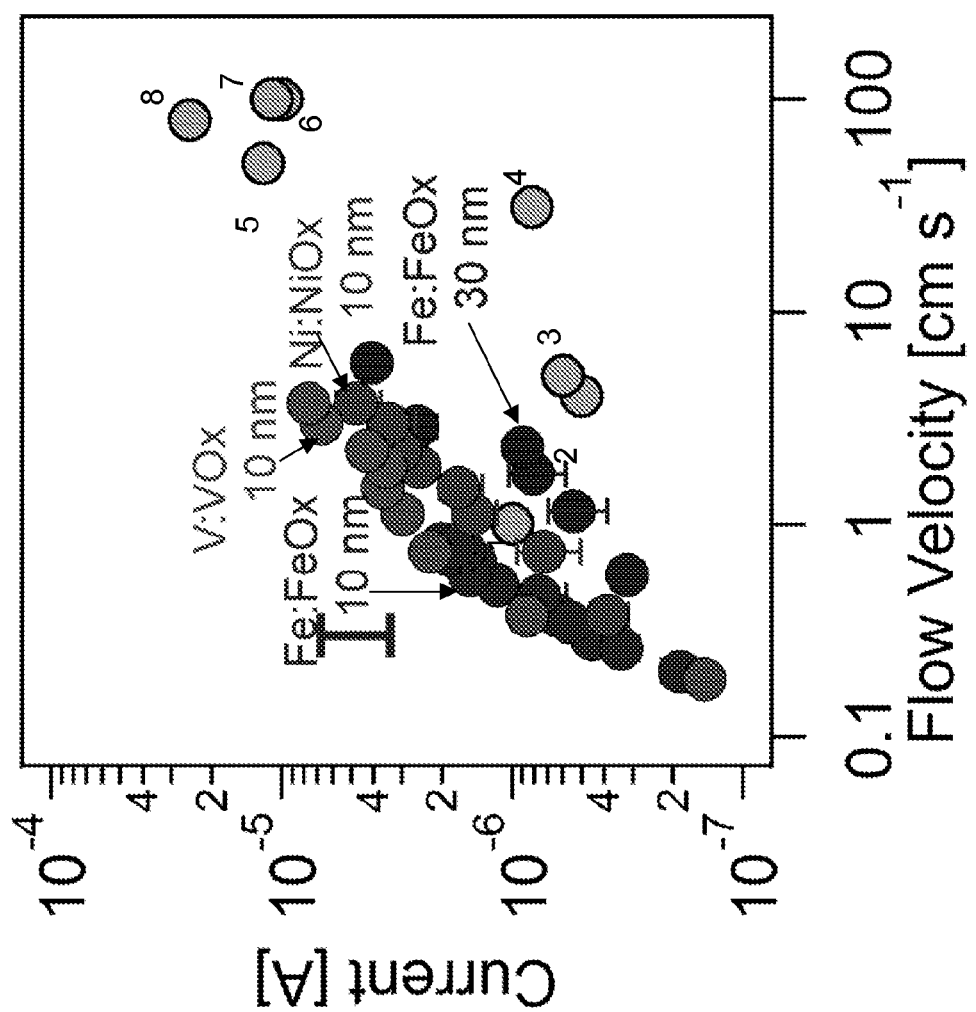
FIG. 10 depicts a plot of FIG. 9B including references provided for the comparison to previously reported results (light grey filled circles). 1=A. T. Liu et al., Advanced Energy Materials 8, 1 802212 (2018); 2=H. Zhong et al., Applied Physics Letters 106, 243903 (2015); 3=J. Park et al., Journal of the American Chemical Society 139, 10968-10971 (2017); 4=Q. Tang, X. et al., Angewandte Chemie International Edition 55, 5243-5246 (2016); 5=G. Zhu et al., ACS Nano 8, 6031-6037 (2014); 6=S. Yang et al., Journal of the American Chemical Society 140, 13746-13752 (2018); 7=Yin et al., Nature Communications 5, 3582 (2014); 8=W. Huang et al., Nanoscale 6, 3921-3924 (2014).
Figure 11:
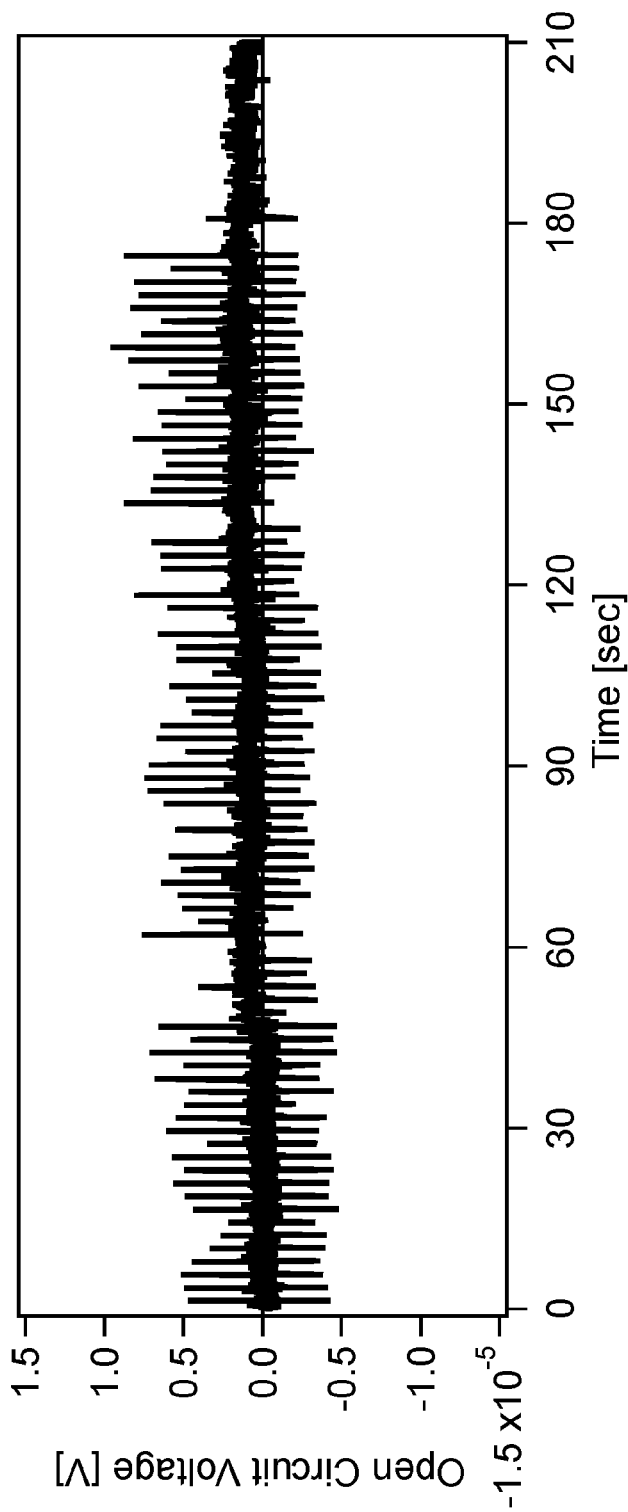
FIG. 11 depicts OCV measured for a 20 nm thin aluminum nanofilm using 600 mM salt (pH 5.8) and a drop rate of 0.5 mL/min.
Figures 12A, 12B:
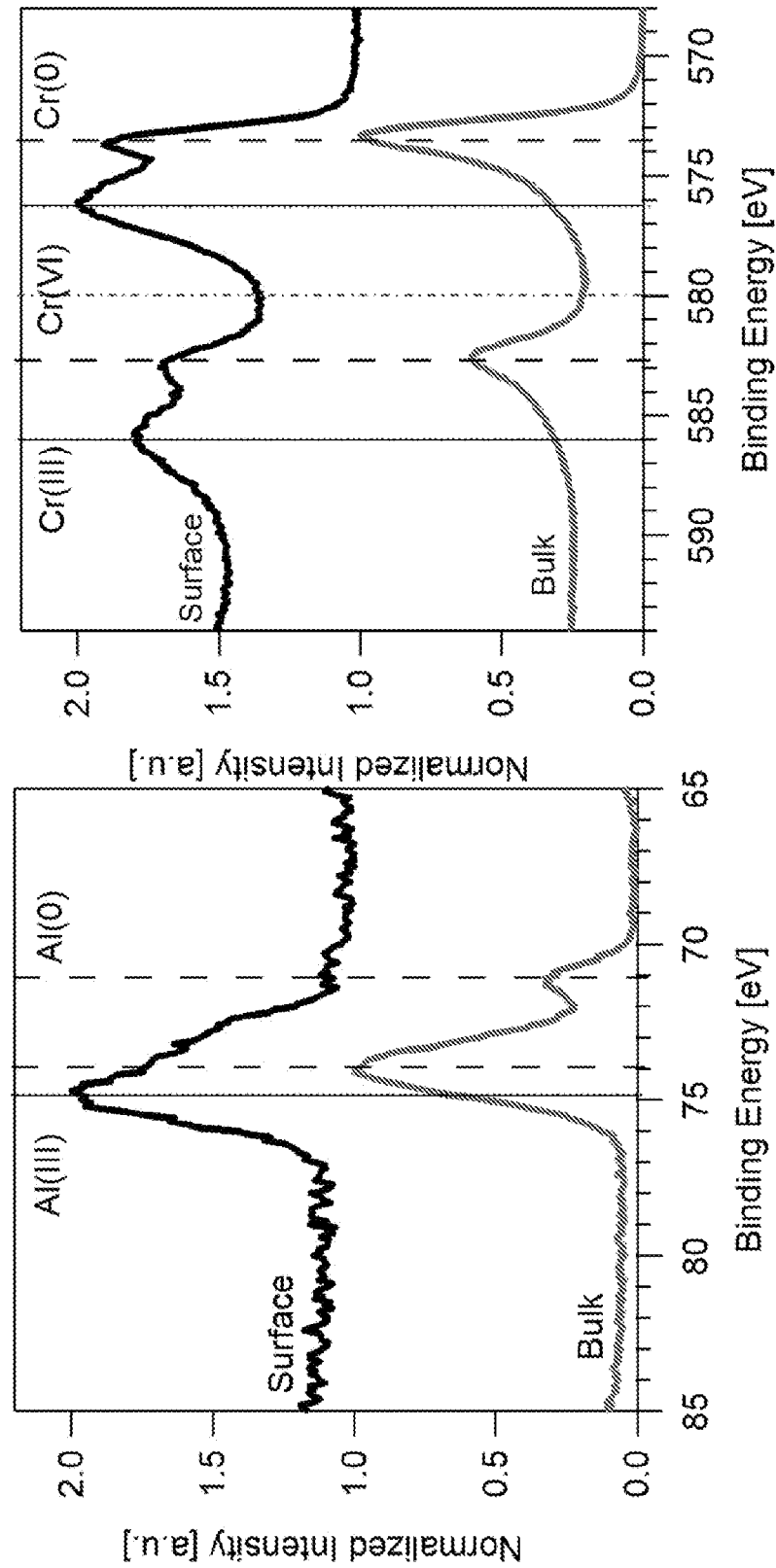
FIGS. 12A-12E depict X-ray photoelectron spectroscopy (XPS) depth profile graphs of ~10 nm (FIG. 12A) Al:AlOx, (FIG. 12B) Cr:CrOx, (FIG. 12C) V:VOx, (FIG. 12D) Fe:FeOx, and (FIG. 12E) Ni:NiOx films deposited on microscope slides. Big and small black dashed lines represent peaks for zero-valent and trivalent/divalent forms of the elements identified, respectively. The dashed vertical line in FIG. 12B shows the absence of hexavalent chromium [Cr (VI)] peaks in the CrOx nano-overlayer. Vertical dotted lines in FIG. 12C show the presence of V(IV) and V(V) in the VOx nano-overlayers, while the dashed lines show V(0). Vertical solid lines in FIG. 12D and FIG. 12E show the presence of M(II) and M(III) in the FeOx and NiOx nano-overlayers.
Figure 12D:
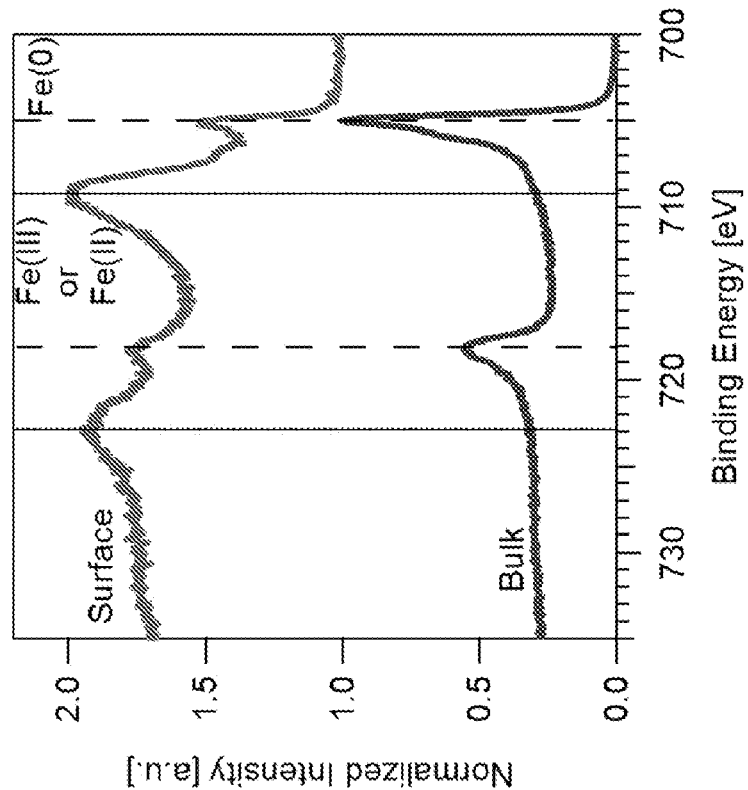
Figure 12C:
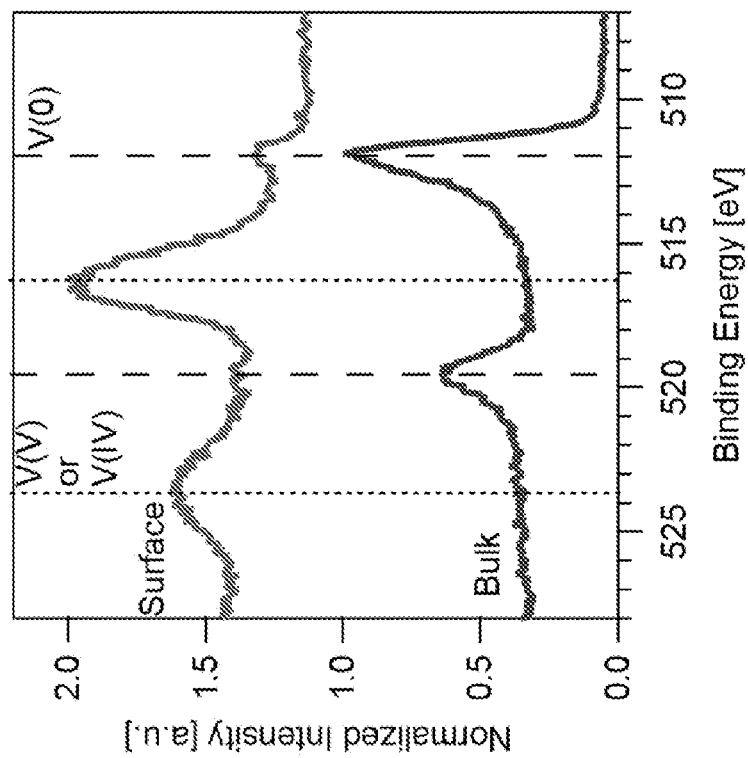
Figure 12E:
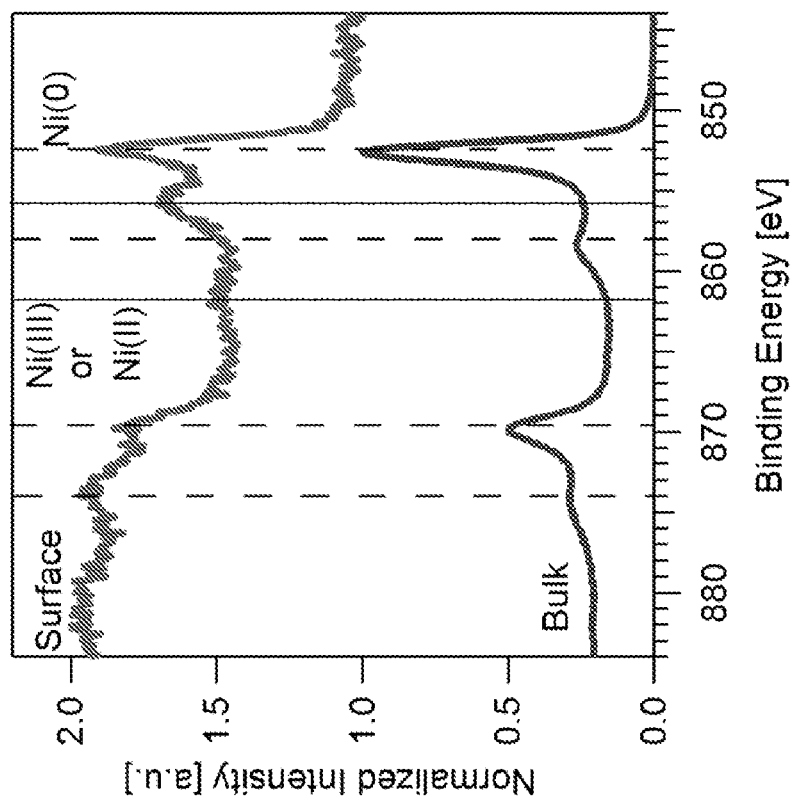

To gain a mechanistic understanding of current generation in the metal nanolayers, a series of experiments were carried out, as described next. FIG. 9A shows that Fe:FeOx, Ni:NiOx, and V:VOx nanolayers of 10 nm thickness produce currents that increase linearly with increasing flow rate at a rate of ~1 to ~3 microA cm$^{-2}$ per cm s$^{-1}$ increase in flow rate. The induced current densities are comparable to what can be achieved with falling water drops (vertical line). The produced currents are also comparable to what has been reported previously but obtained with considerably lower flow velocities when using 10 nm or 30 nm thin iron nanolayers or 10 nm thin nickel nanolayers (FIG. 10). (J. Yin et al., *Nature Nanotechnology* 9, 378-383 (2014); and J. P. G. Tarelho et al., *Mat. Today* 21 (2018).) Given that the iron oxide nano-overlayers contain iron in multiple oxidation states, it was then investigated whether metal nanolayers terminated with redox-inactive oxides would produce smaller currents. Indeed, FIG. 9A shows that 10 nm thin metal nanolayers prepared from Cr and Al produce considerably less current than 10 nm thin nanolayers prepared from Fe, Ni, or V at comparable flow conditions. FIG. 11 shows a 20 nm Al:AlOx nanolayer also produces considerably less open circuit potential than the Fe:FeOx, Ni:NiOx, or V:VOx layers of comparable thickness. These results are rationalized by the observation that the iron, vanadium, and nickel nanolayers are terminated by thermal oxides that contain Fe(II) and Fe(III), V(IV) and V(V), and Ni(II) and Ni(III), respectively, whereas the aluminum and chromium metal nanolayers are terminated by thermal oxides that only contain metal in the +3 oxidation state (FIGS. 12A-12E).

The absence of metal results in negligible current, as shown in FIG. 9B for a 10 nm thin nanolayer of FeOx (no Fe(0) present) prepared by high-temperature quantitative ozone oxidation of a 10 nm thin nanolayer of Fe:FeOx. FIG. 9C shows that a 10 nm thin Fe:FeOx structure produces the highest currents when compared to thinner (5 nm) or thicker (30 nm and 50 nm) layers.

Figure 9D:
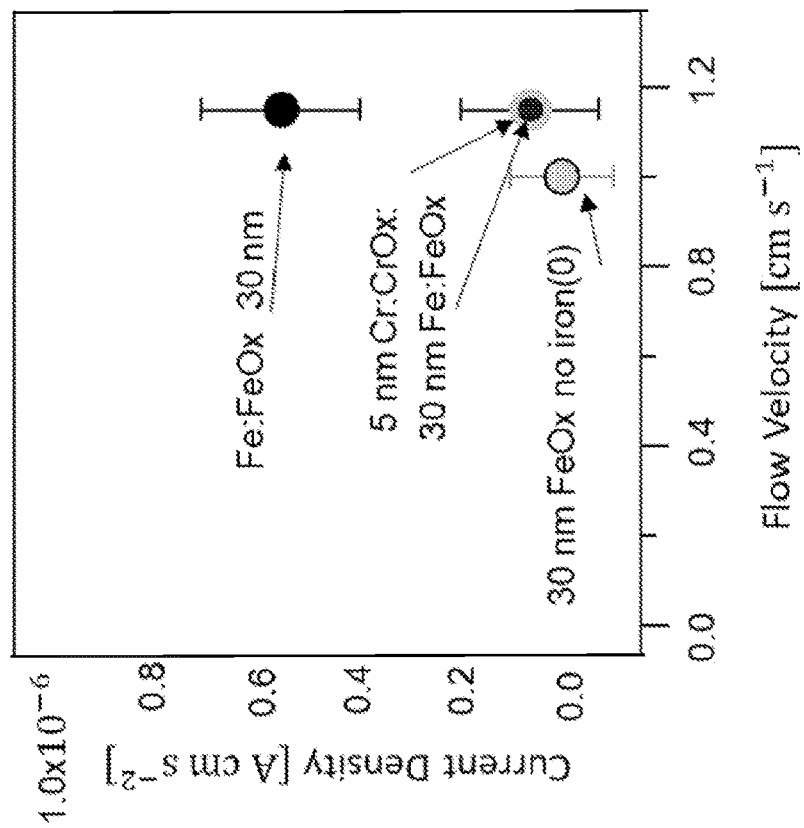
Figure 9C:
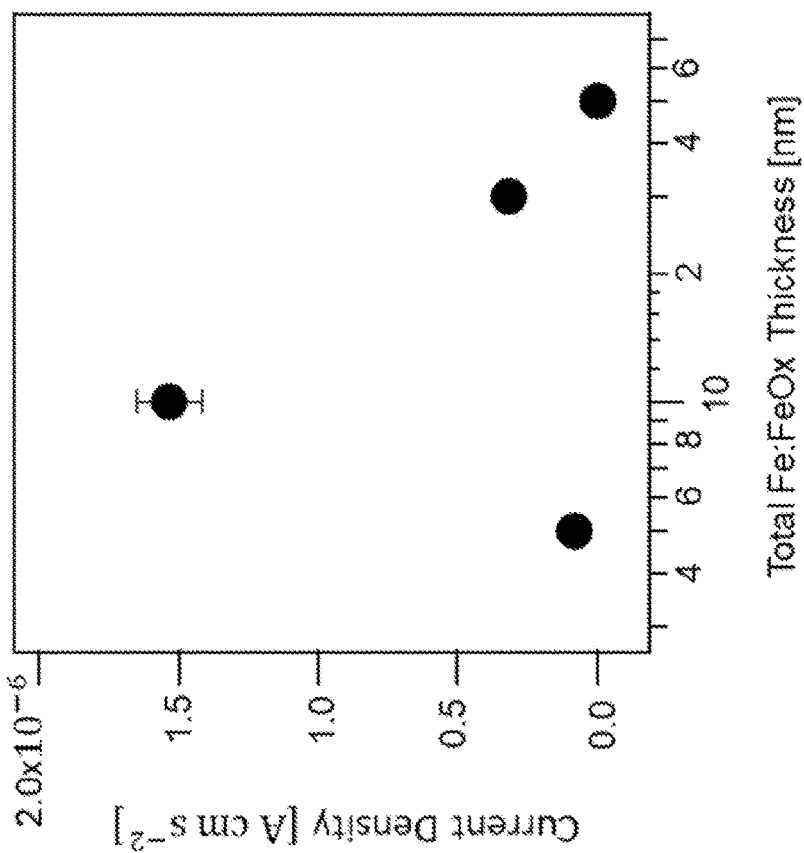
Figure 9F:
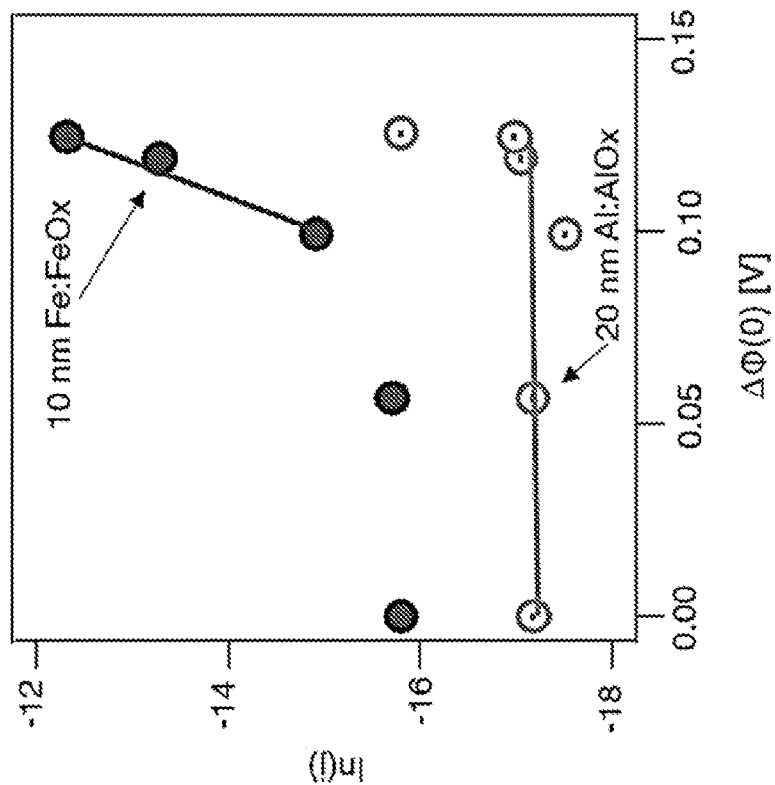
Figure 9E:
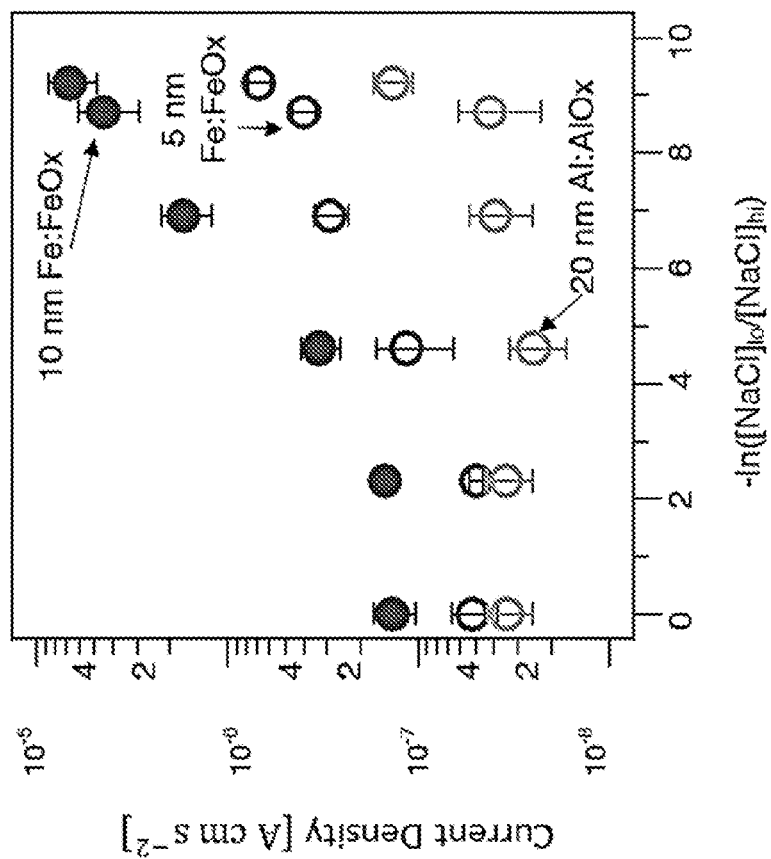

Given the results with the six different systems described in FIGS. 9A-9B, it is expected that covering an active nanolayer (Fe:FeOx or Ni:NiOx) with a less active one (Al:AlOx or Cr:CrOx) should diminish the current density. Indeed, coating a 30 Fe:FeOx nanolayer with 5 nm Cr:CrOx results in considerable current reduction when compared to the neat Fe:FeOx nanolayer (FIG. 9D).

Taken together, the data shown in FIGS. 9A-9D demonstrate that intra-oxide electron transfer between M$^{m+}$ and M$^{n+}$ contributes to the current generation to a larger extent than would be expected from image charge formation alone in metal layers terminated by a redox inactive thermal oxide. Moreover, it is expected that current generation can be further optimized by varying the nature and thickness of the metal and metal oxide layers in mixed metal architectures, alloys, or patterned nanolayers.

The experiments described here additionally support the notion that surface charging of the metal oxide surface is an important part of the current generating mechanism in the metal nanolayers reported here. To explore this hypothesis, the electrical current was recorded as a function of the change in surface potential that occurs when changing the ionic strength from low to high salt concentration. To do so, the current was measured while changing the ionic strength from a given low salt concentration, for example, 0.1 mM, to 1 mM salt for several cycles, and then repeated those measurements for increasingly higher salt concentrations, each time starting at 0.1 mM (FIG. 9C). The largest currents are induced when the ionic strength difference is largest for each system studied. Experimental surface charge density estimates from second harmonic generation $\chi^{(3)}$ measurements were then used to compute the change in Gouy-Chapman surface potential at the oxide/water interface for each ionic strength difference. FIG. 9D shows that the slopes in these "Tafel" plots are 110 (+/-20) V$^{-1}$ for the Fe:FeOx system. The Al:AlOx system, which is redox inactive under the conditions of these experiments, shows a slope of 7 (+/-2) V$^{-1}$ for all Gouy-Chapman surface potential differences surveyed except the highest, underscoring the large differences between the surface charging of the Al:AlOx and Fe:FeOx nanolayers.

Figure 13:
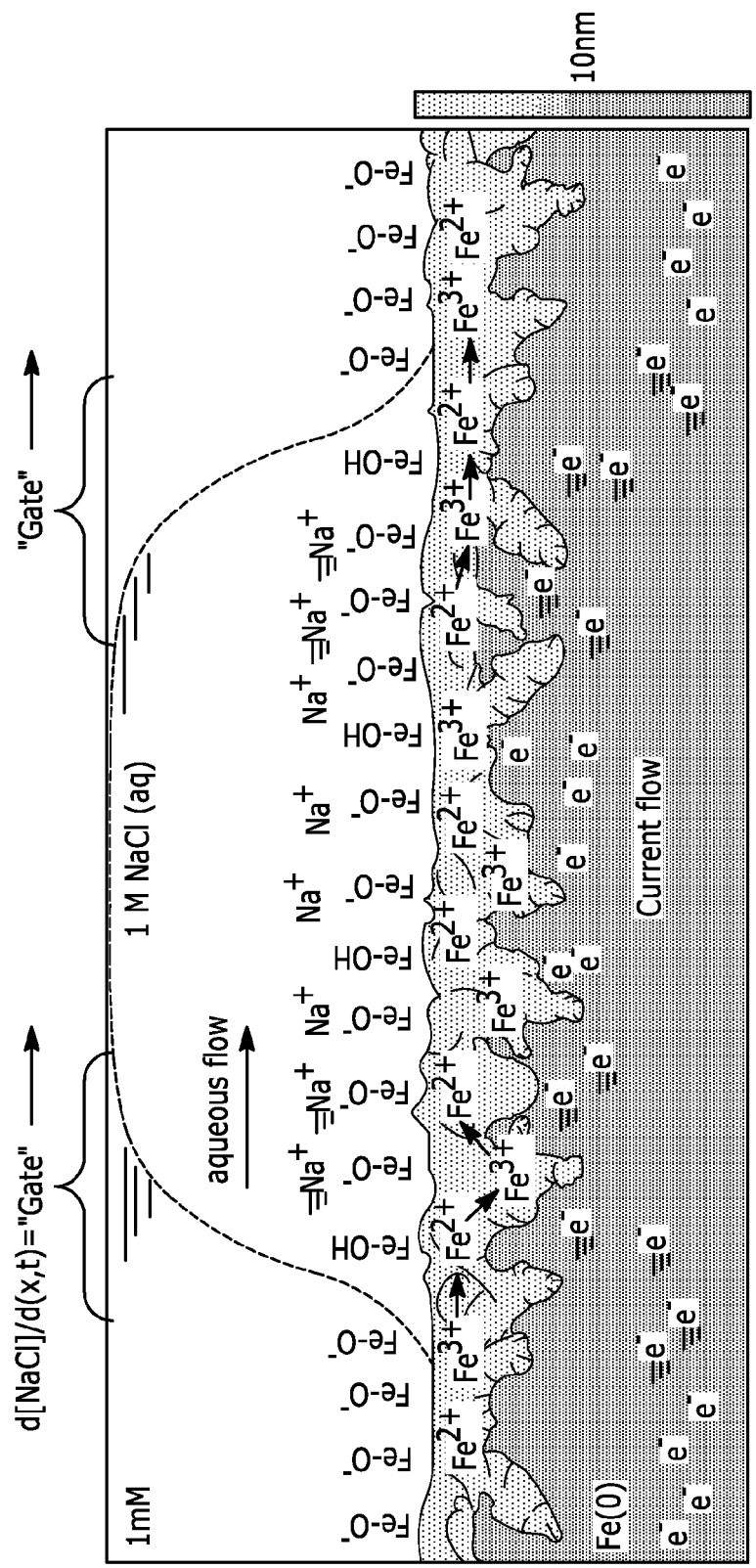
FIG. 13 is a cartoon representation of electrical energy conversion in metal nanolayers terminated by their thermal oxides.
Figure 14A:
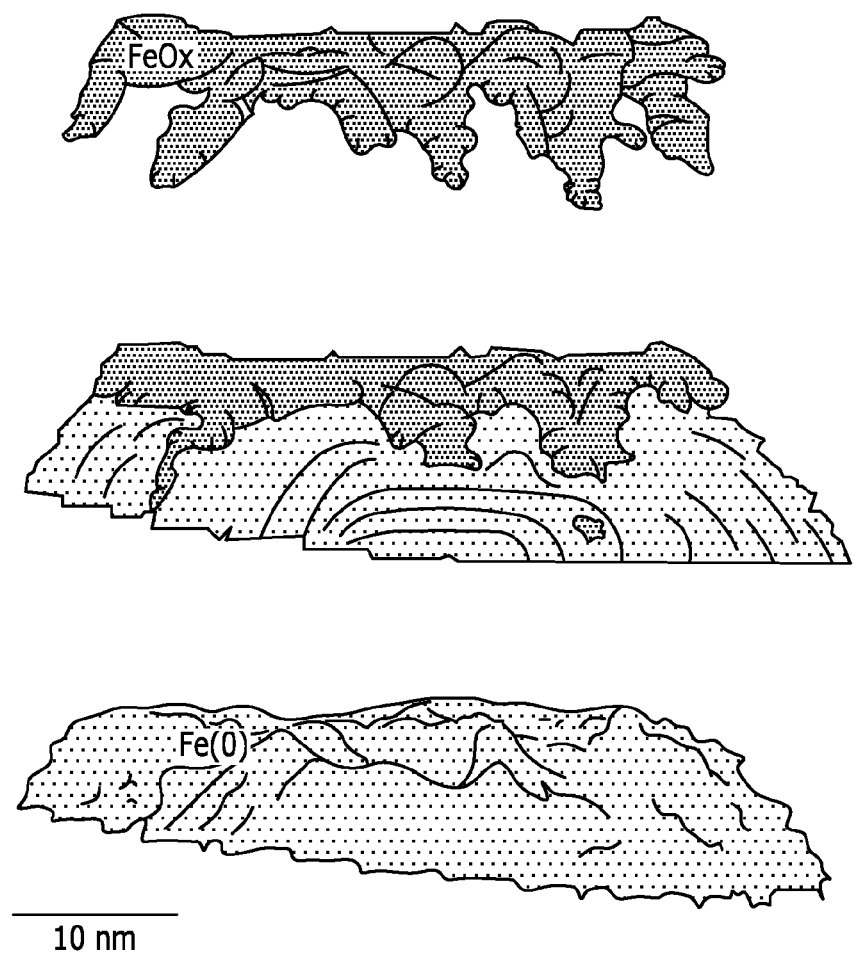
FIGS. 14A-14G: Model of Charge Mobility in a Nano-confined, Insulator-Terminated Metal Conductor.

Zooming out, FIG. 13 offers the following phenomenological interpretation of these findings, followed by a detailed microscopic investigation below. At the pH values used here (5.8 for low- and 8.0 for high-salinity water), the water:oxide interfaces that were investigated are charged. The electrostatic potential reaches not only into the aqueous solution but also into the oxide, depending on the local dielectric properties. Thus, if the oxide nano-overlayer is thin enough, the electrostatic potential extends beyond it to polarize the underlying metal, similar to metal atom charging on ultrathin oxides by underlying metals or the phenomenology of the Cabrera-Mott model. Given the presence of different oxidation states in the iron, vanadium, and nickel oxide nano-overlayers, conduction by intra-oxide electron transfer, like what is known from bulk hematite crystals or from chemical reactions on nanolayer metal-semiconductor heterostructures, is likely to be important as well. Electrical current is then generated by moving an EDL gradient (a "gate") across the metal:metal oxide nanolayer to drive electron transfer within the oxide nano-overlayer, which is coupled to the underlying metal nanolayer. The sharper the gradient, the larger the current density, j. Dendritic iron oxide features of ~5 nm×~10 nm size (FIG. 14A) that extend from the surface into the bulk of the iron metal nanolayer, as revealed by APT, open possibilities for an electron and/or hole ratchet, similar to what has been proposed for low-light energy-driven transducers, or pose limits due to tunneling losses. Structures whose oxide nano-overlayers contain only a single oxidation state, such as those formed from Al or Cr metal, should still produce currents due to contact electrification, but the lack of intra-oxide electron transfer would diminish their current output.

The system presented here differs in several aspects from recent demonstrations of flow-induced power generation. First, the experiments described here are consistent with a mechanism for electrical current generation that involves redox activity in the metal oxide layer. Second, the all-inorganic devices described here are composed of metal nanolayers formed on a given support in a single step over arbitrarily large areas using an electron beam deposition apparatus. Upon exposure to ambient air, an oxide nano-overlayer forms spontaneously and then self-terminates after ~3 to ~5 nm, depending on the thickness of the underlying metal nanolayer. The high purity of the metal nanolayer prevents further growth of the oxide nano-overlayer, resulting in a stable structure. Third, the amphoterism of the thermal oxide nano-overlayer is critical to EDL gradient, or "gate", formation as solutions move across the liquid:solid interface. Fourth, the thickness of the metal nanolayer needed to produce current (FIG. 9C) is comparable to the mean free path of the electrons in it, engendering a propensity for charge motion parallel to as opposed to away from the interface. Fifth, the starting materials, a suitable support, and a standard-purity metal source (Fe, Ni, V, Al, Cr, etc.), are inexpensive.

Figure 14B:
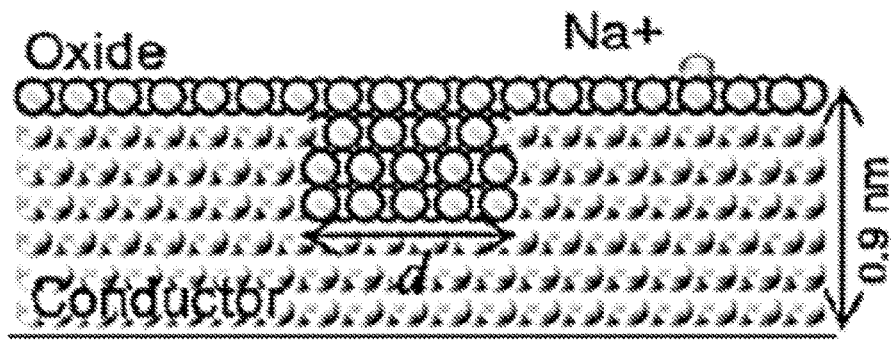
Figure 14C:
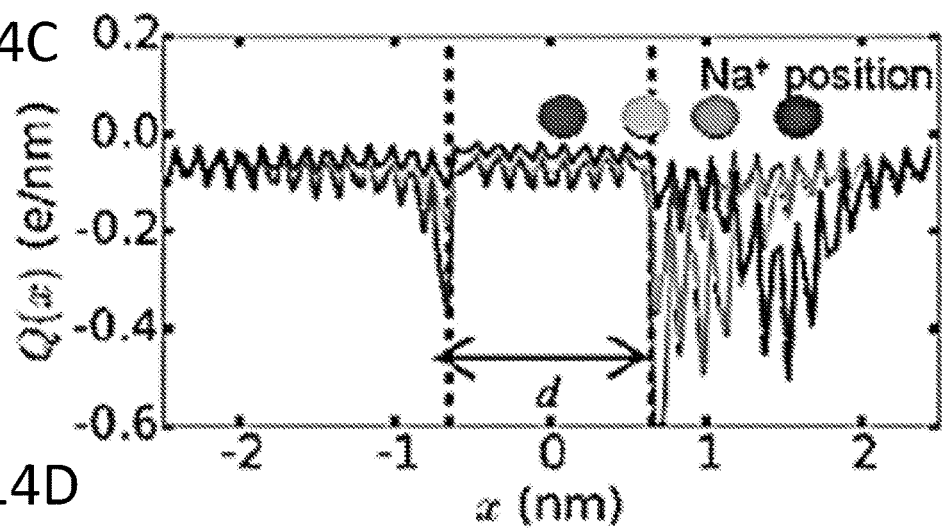
Figure 14D:
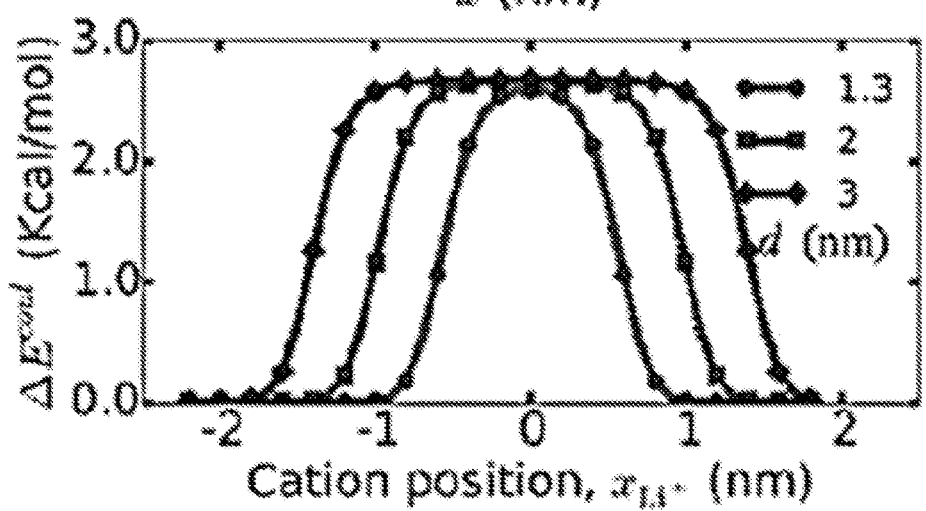

To probe the charge fluctuations in the metal:metal oxide (M:MOx) nanolayer in the presence of moving ions, calculations were performed using an all-atom MD model for the solvent, ions, and a M:MOx nanolayer, including charge-polarization of the nanolayer and image-charge interactions between the nanolayer and the solution. The M:MOx nanolayer is modeled after the APT reconstruction of the Fe:FeOx nanolayer (FIG. 14A) as a polarizable metal conductor (FIG. 14B) with a non-polarizable oxide heterostructure. The subsurface metal/oxide heterostructure is modeled in a simple columnar geometry with a range of values for the width, d. For a given width of the oxide heterostructure (d=1.3 nm), FIG. 14C illustrates the distribution of induced charge in the nanolayer for several positions of a sodium cation. Substantial polarization of the metal for ion positions away from the nonpolarizable heterostructure is reduced when the cation is positioned above the heterostructure (FIG. 14C and FIGS. 15A-15D). This position-dependence of the induced charge manifests in the Coulomb interaction between the ion and the nanolayer (FIG. 14D), leading to a heterostructure-dependent interaction potential between the M:MOx nanolayer and the ion, with a potential energy barrier appearing in the region of the nonpolarizable heterostructure.

Figure 14E:
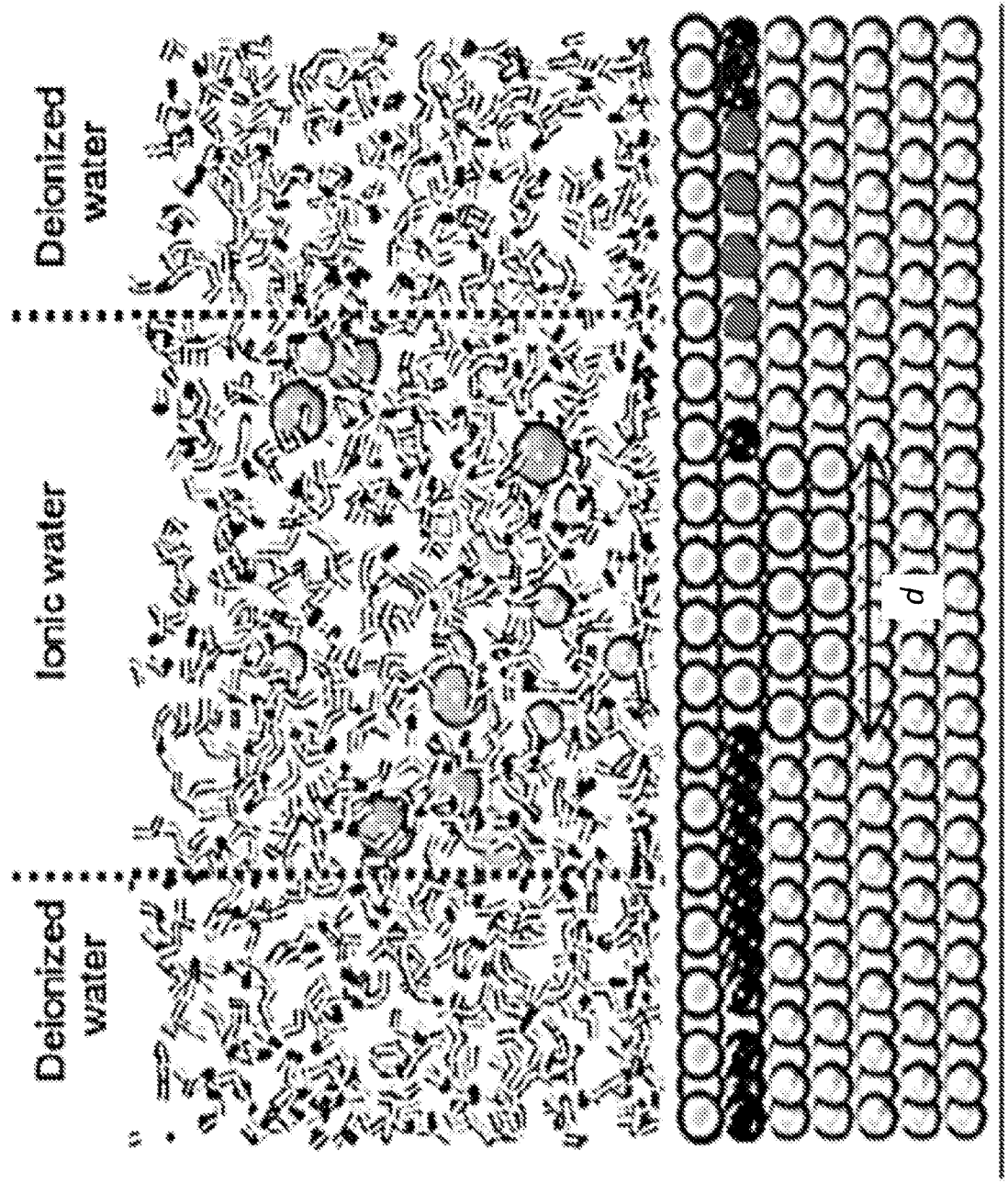
Figure 14F:
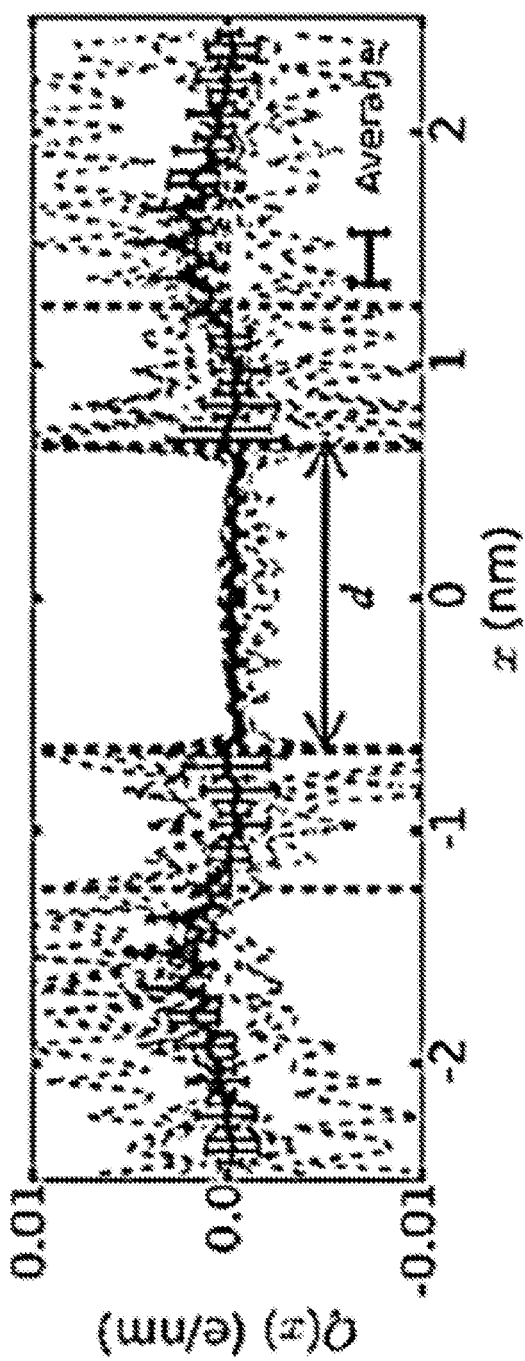
Figure 14G:
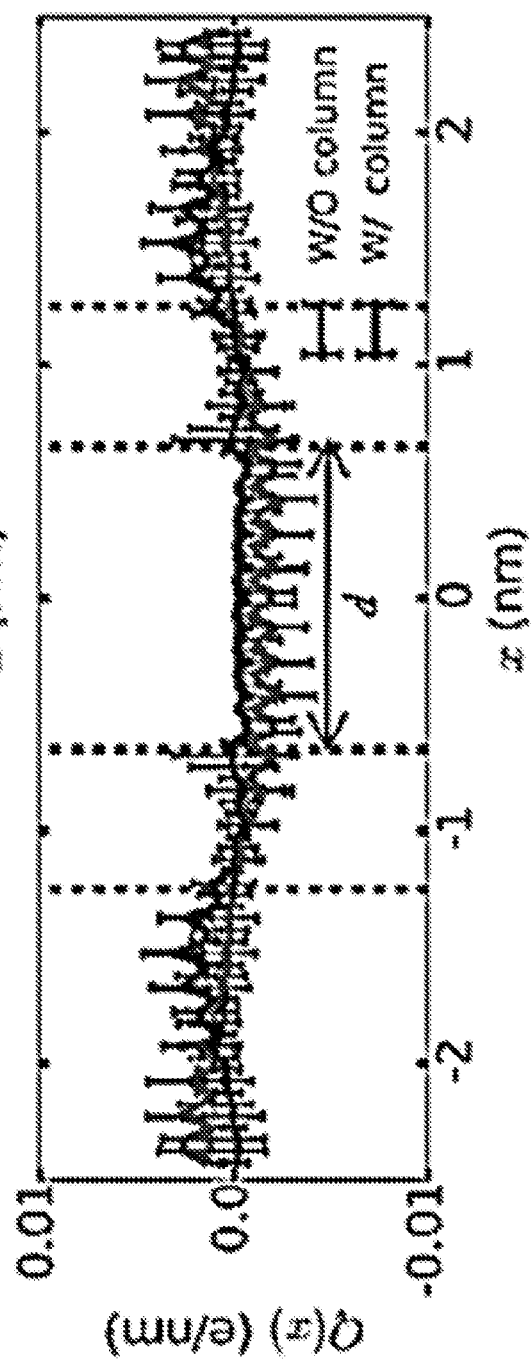
Figures 15A, 15B, 15C, 15D:
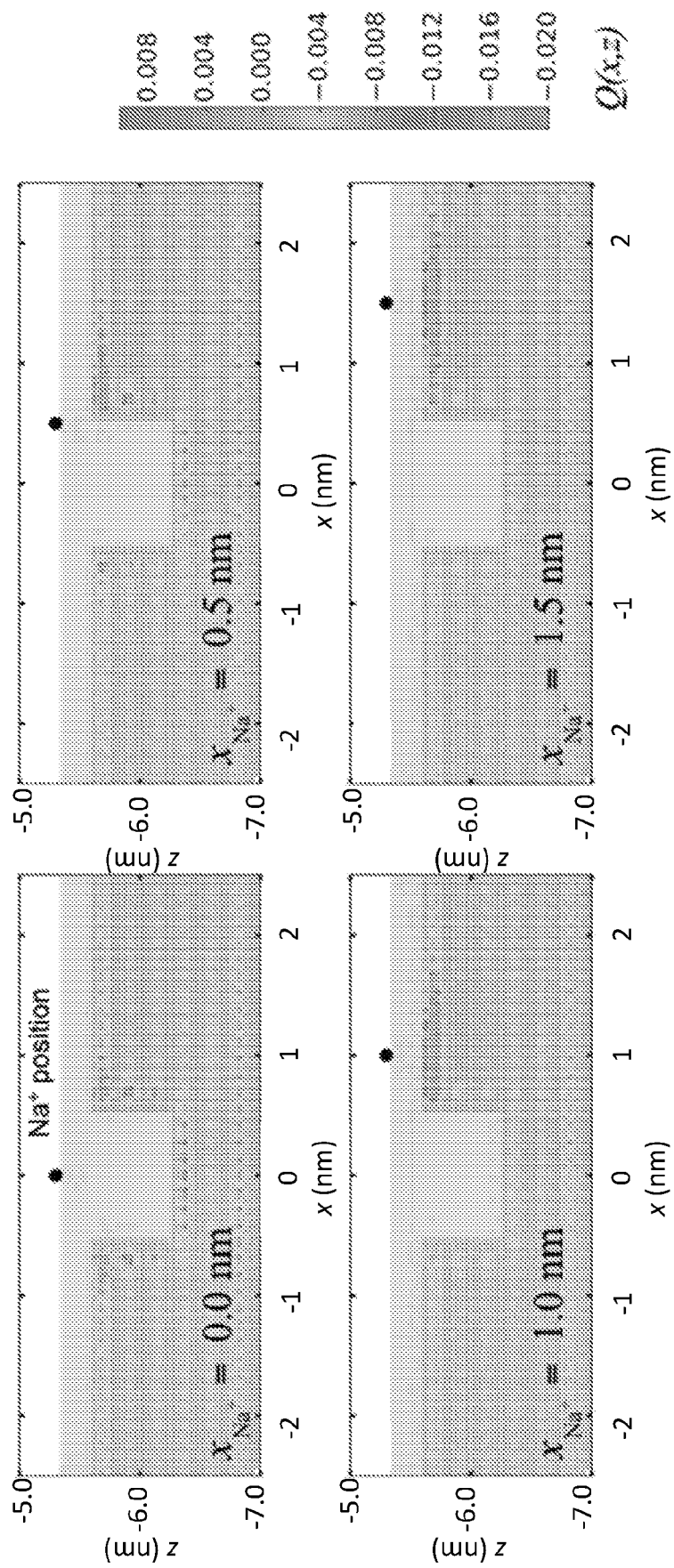
FIGS. 15A-15D depict, for various positions of a single monocation, the distribution of induced charge in the metallic portion of the nanolayer, Q(x,z), integrated over the y-coordinate of the simulation cell. Nonpolarizable oxide atoms are indicated with darker, solid grey shading. The position of the monocation is indicated with the black circle, illustrating various displacements with respect to the position of the subsurface heterostructure.

To examine these nanolayer polarization effects in the presence of a solution with alternating salinity, FIG. 14E shows a snapshot of all-atom MD simulations, with vertical lines indicating semipermeable boundaries for the solvated ions and with the instantaneous induced charge fluctuations on the electrode shown in greyscale. FIG. 14F shows the time-averaged charge induced charge distribution for the shown simulation cell, as well as 0.5 ns block-averages of the distribution. Two features are immediately clear: (i) the induced charge distributions in the metal/oxide nanolayer undergo dramatic fluctuations with changes of the ion and water configuration, which reflect changes in the transient electrostatic interactions between the nanolayer and the solvated ions, and (ii) these induced charges are massively damped out in the vicinity of the nonpolarizable heterostructure, i.e., the oxide nano-overlayer. FIG. 14G shows that the effect of the heterostructure on the average induced charge is much smaller than its effect on the fluctuations.

The simulations in FIGS. 14F-14G reveal that the nonpolarizable heterostructure model of the metal oxide nano-overlayer creates spatial variation in the local induced charge fluctuations in the metal nanolayer below. These fluctuations are proportional to the local interfacial capacitance, i.e., $C_F = \beta \langle (\delta Q(x))^2 \rangle$. Given that this interfacial capacitance connects droplet motion to induced current, $$I = -\psi \frac{dC_F}{dt}$$

where $\psi$ is the surface potential, the simulations thus provide a direct connection between the morphology of the oxide heterostructure and the gate-induced current presented here. Moreover, these simulations reveal that the interfacial capacitance that gives rise to the current is strikingly sensitive to the electronic character and spatial features of oxide heterostructure, such that nanometer-scale changes in the heterostructure give rise to unexpectedly large effects in the resulting interfacial capacitance.

The effects observed in the simulations are expected to be further enriched by the amphoterism of the oxide overlayer, which is important for determining the sign and magnitude of the charge and potential distributions within the EDL under conditions of varying aqueous pH and ionic strength. Control over the structure of the oxide dendrites, their number density, and their width and depth offers the possibility to further optimize charge mobility along the potential hotspots on the dendrites and minimize possible leakage due to tunneling. Additional control comes from the choice and concentration of ions in the aqueous phase and the steepness of the salt concentration gradient, which determines the area of the gate footprint at the aqueous/solid interface (steeper gradients lead to increased current densities, j). Moreover, the volcano plot-like current vs. M:MOx film thickness data shown in FIG. 9C suggests that film thickness on the order of the mean free path of the electron is desirable for current generation, offering an additional means of optimizing the electron current flow.

Figure 16:
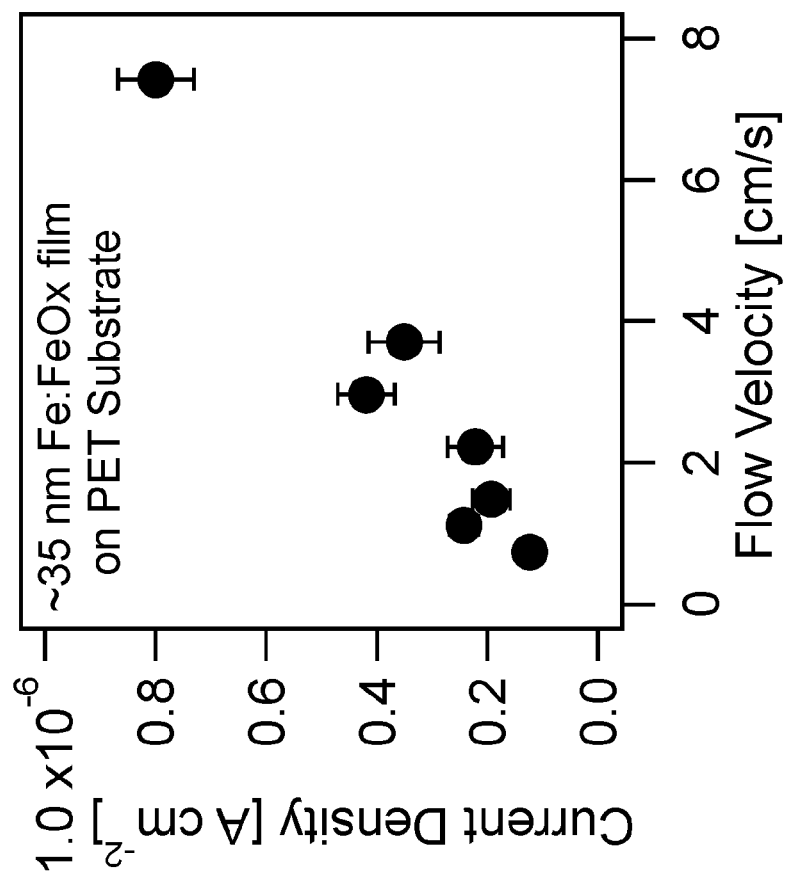
FIG. 16 depicts current density vs. flow velocity for a ca. 35 nm thin Fe:FeOx nanolayer on a poly(ethylene) terephthalate (PET) substrate obtained when alternating DI water and 1 M NaCl solution segments every 20 sec.

The relatively modest flow velocities surveyed here (a few cm s$^{-1}$) indicate the approach presented here may work in entirely passively operating assemblies, yet there is ample room for improvement. The use of appropriate metals having biocidic properties (Al, Zn, Ag, Cu) may have the additional benefit of counteracting biofilm formation in the field. The optical properties of the iron and nickel nanolayers also open the possibility of further charge carrier generation by visible light, conversion boosting of solar cells, or the coating of building windows with the nanolayers, given the ionic strength of rainwater (0.2 mM) and the low absorbance of the nanolayers in the visible spectrum. PVD onto plastics or flexible substrates (FIG. 16) also allows for large-area yet light-weight and/or foldable designs. PVD of appropriately formulated metal nanolayers into tubes allows for implantable applications in vivo, while PVD of metal nanolayers onto a range of other polymers surveyed opens the door to transducers operating in three-dimensional structures prepared, for instance, by 3D printing.

A plurality of the devices described herein could be connected for increased power generation. By way of example, a set of 100 connected devices of 10 m$^2$ area could be connected to generate 2 kW hours, or more, using an ionic solution with a temporally varying the salinity at 10 Hz. This estimate is based on measured observations of approximately 30 microWatt g$^{-1}$ water m$^{-2}$ per salinity alternating event according to an external load resistance of 100 kOhm.

Figures 17A, 17B:
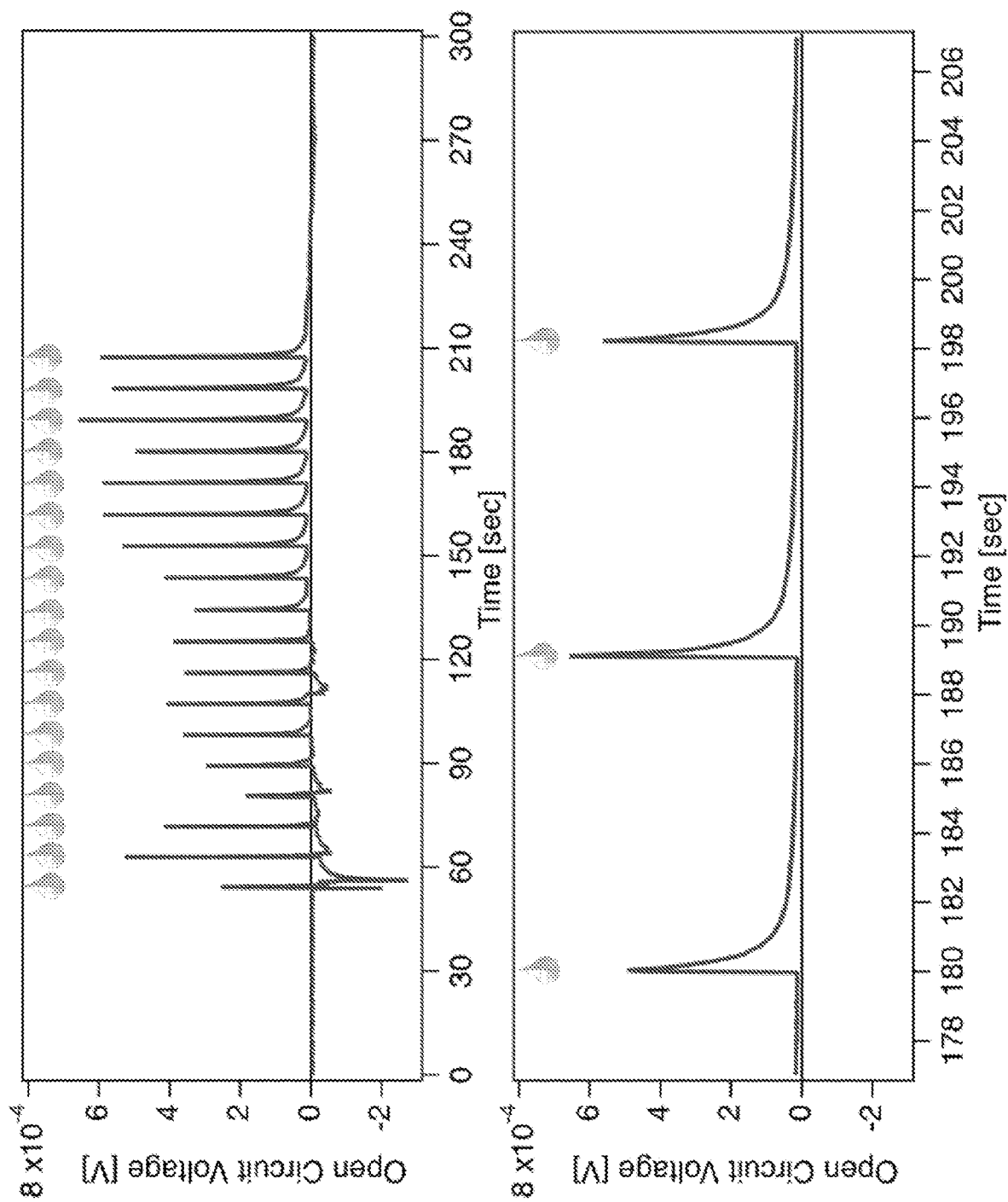
FIGS. 17A-17B depicts OCV measured for a freshly prepared 10 nm thin iron nanofilm using 100 mM salt and a drop rate of 0.5 mL/min (FIG. 17A) and zoomed in to show three voltage spike events (FIG. 17B).

Methods. The nm-thin iron layers and their oxide nano-overlayers were prepared on glass microscope slides (VWR) and characterized as described in previous work. (Faurie-Wisniewski, D., et al., *The Journal of Physical Chemistry C* 118, 23256-23263 (2014); and Boamah, M. D. et al., *arxiv:* 1809.04909 (2018).) Computer controlled multi-channel Ismatec peristaltic pumps (ISM4408) were used. Aqueous solutions were prepared from NaCl (Sigma-Aldrich) in Millipore water adjusted to pH 7 or equilibrated with ambient air to pH 5.8 and containing various amounts of NaCl, as indicated in the Brief Description of the Drawings. "Instant Ocean Aquarium Sea Salt" was used as received from Amazon (ASIN: B00NQH210G). The drop experiments were performed using motorized syringe pumps (Harvard Apparatus Elite 11). Using Teflon tubing, drops having an average volume of 0.0165 (1) mL (measured for a flow rate of 0.5 mL/min) were released in ambient laboratory air from a height of 10 cm onto a given device held in air by an electrically insulated clamp at an incident angles of ~20 degrees. Variations in incident angle, drop release height, and drop size led to variations in drop flow dynamics and velocity on the nanolayer surfaces and corresponding variations in magnitude and duration of the measured open circuit voltage spikes, similar to what had been reported in the earlier studies using carbon- and semiconductor structures that are mentioned above. Nanolayers stored for prolonged periods of time (~two years) in ambient laboratory air showed larger contact angles (Computerized First Ten Ångstroms contact angle goniometer, $\theta=57\pm5°$ from seven replicates using DI water) than freshly prepared nanolayers ($\theta$=37±3° from seven replicates using DI water), on which the water drops spread considerably more while also producing open circuit potential spikes that are somewhat larger in magnitude and longer in duration (FIGS. 17A-17B). Given the potential relevance of the system described here for use in the ambient environment, the results from nanolayers that had been stored in the dark for about two years in conical centrifuge tubes made of polypropylene (Falcon, 50 mL, with screw top) containing ambient air are emphasized here. Drops rolling off the device were collected in a receptacle. Open circuit potential measurements were performed using a Keithley 2100 voltmeter and standard alligator clip-on probes, taking special care to keep the probes dry. The resistance of the dry nanolayers was around 50 to 500 Ohm (Keithley 2100), depending on layer thickness. Short circuit current measurements were carried out on an Agilent B1500A semiconductor parameter analyzer equipped with a high-resolution SMU and on a Keithley 6485 Ammeter.

XPS. XPS depth profile measurements were carried out with a Thermo Scientific ESCALAB 250 Xii instrument stationed at the NUANCE center at Northwestern University. The instrument is calibrated to the Au $4f_{7/2}$ line at 83.96 eV. It uses a K$\alpha$ radiation from a monochromatic aluminum source. A flood gun is used for the ejection of low energy $Ar^+$ ions and electrons to compensate for surface charging. The 2 mm raster size 2 keV etching mode ion (AO gun at mid current was employed to prevent the reduction of trivalent ions to divalent ions.

The results are shown in FIGS. 12A-12E. The physical-vapor deposited aluminum nanolayers show Al(III) species in the oxide nano-overlayer, and the bulk is Al(0). For chromium nanolayers, XPS peaks indicate the presence of Cr(III) oxides in the oxide overlayer, and the bulk is Cr(0). Iron nanolayers were characterized with Raman spectroscopy, XRD, APT, and XPS in recent publications. (Boamah, M. D. et al., *The Journal of Physical Chemistry C* 122, 28225-28232 (2018); and Faurie-Wisniewski, D. et al., *The Journal of Physical Chemistry C* 118, 23256-23263 (2014).) Iron nanolayers have nano-overlayers containing magnetite and hematite, protecting the Fe(0) bulk. XPS peaks of nickel nanolayers indicate the presence of both Ni(III) and Ni(II) oxides on the surface, while the bulk is Ni(0). For vanadium, V(V)/(IV) oxides are on the surface, while the bulk is V(0).

Computational methods. Molecular dynamics simulations were performed using a polarizable model for the conductive regions of the iron nanolayer. In these simulations, possible redox activity in the oxide layer was not accounted for; instead, it was simply modeled as an insulator. The atoms in the nanolayer were fixed in the face-centered cubic structure with a lattice parameter of 0.392 nm and a (111) termination at the interface. The orthorhombic simulation cell was oriented such that the z coordinate was perpendicular to the nanolayer surface, the x coordinate coincided with the direction of the gate motion, and the simulation cell was periodically replicated only in the x and y coordinates. In all simulations, the length of the simulation cell in the x and y coordinates was 4.979 nm and 4.791 nm, respectively, such that the nanolayer was described using seven layers of atoms, with each nanolayer layer containing 360 atoms (for a total of 2520 nanolayer atoms). Atoms in the nanolayer were modeled as being either oxide-like (i.e., non-polarizable) or metallic (i.e., perfectly conductive). In all simulations, the top layer of atoms in the nanolayer was assumed to be oxide-like, and the arrangement of oxide-like atoms below the nanolayer surface was varied to model the subsurface heterostructure, as described.

Interactions between atoms in the nanolayer and other atoms in the simulation cell are described using both electrostatic and Lennard-Jones (U) interactions. Oxide-like atoms in the nanolayer were uncharged, while the charges of the metallic atoms of the nanolayer were allowed to fluctuate in response to charges in the solution. The metallic portion of the nanolayer was modeled as one of two fixed-potential electrodes with zero potential bias, with the fluctuating charge distribution in the metallic portion of the nanolayer described in terms of a sum of atom-centered spherical Gaussian functions, $$Q_i(r, t) = A_i(t) * \left(\frac{\eta^2}{\pi}\right)^{3/2} \exp[-\eta^2(r - R_i)], \quad \text{Eqn. S1}$$

of width $\eta$=19.79 $nm^{-1}$ and amplitude $A_i(t)$ that was determined using an extended Lagrangian method. (J. I. Siepmann et al., *J. Chem. Phys.* 102 (1995).) Although all calculations involving the iron nanolayer focused on a single solid/liquid interface, the fixed-potential electrode simulation model required that two electrodes be included in the simulation cell; the second polarizable electrode was simply placed a large distance from the interface of interest, separated by ~10 nm of vacuum in the z coordinate. All simulations were performed using the LAMMPS software package. (S. Plimpton, *J. Comp. Phys.* 117, 1-19 (1995).)

Nanolayer/liquid interface MD simulations. Simulations of aqueous solutions in contact with the nanolayer were performed using SPC/E water and NaCl ions. (H. J. C. Berendsen et al., *J. Phys. Chem.* 91 (1987); and D. E. Smith, et al., *J. Chem. Phys.* 100 (1994).) LJ parameters for the Na+, Cl−, and nanolayer atoms are provided in Table 1. The cross terms were obtained using Lorentz-Berthelot mixing rule. The LJ interactions and the real-space part of the Coulomb interactions were truncated at 0.98 nm; the long-range contribution of Coulomb interaction was treated by the particle-particle particle-mesh method. (R. W. Hockney, et al., Raylor & Francis, New York, NY, 1989.) Via these LJ interactions, the oxide surface preferentially interacts with the $Na^+$ cations over the $Cl^-$ anions.

TABLE 1

Lennard-Jones parameters for water, ions, and nanolayer atom.

| | $\sigma$ (nm) | $\epsilon$ (kcal/mol) |
|---|---|---|
| $Na^+$ | 0.235 | 0.13 |
| $Cl^-$ | 0.44 | 0.1 |
| O (SPC/E water) | 0.3166 | 0.1554 |
| Nanolayer atom | 0.2534 | 0.078 |

To enforce the regions of alternating salinity in the solution (FIG. 13), semipermeable boundaries are introduced to interact only with the NaCl ions; the boundaries are positioned at x=1.25 nm and x=−1.25 nm in the simulation cell, and they interact only with the salt ions via a truncated LJ potential with epsilon=10 kcal/mol and sigma=cutoff=0.1 nm. Simulations of the solution/nanolayer were initialized with a slab of water/ions in contact with the nanolayer; after a short period of equilibration, the outermost layer (furthest from the nanolayer) was frozen in space to provide a fixed, amorphous boundary between the solution region and the vacuum of the remaining simulation cell. Finally, the distance between this fixed layer of water molecules and the position of the nanolayer was adjusted so that the pressure of the confined solution was 1 atm, and it was confirmed that the osmotic pressure introduced by the semipermeable boundaries did not significantly alter the density of water in the ionized vs. deionized solution regions. The final thickness of water along the confinement was ~3 nm.

The classical molecular dynamics equations of motion were evolved using the velocity Verlet integrator with a timestep of 2 fs; rigid-body constraints for the water molecules were enforced using the SHAKE algorithm. (J.-P. Ryckaert et al., *J. Comp. Phys.* 23 (1977).) The simulations were performed at a temperature of 298.15 K, enforced via the Nosé-Hoover thermostat with a damping timescale of 100 timesteps.

Figure 18:
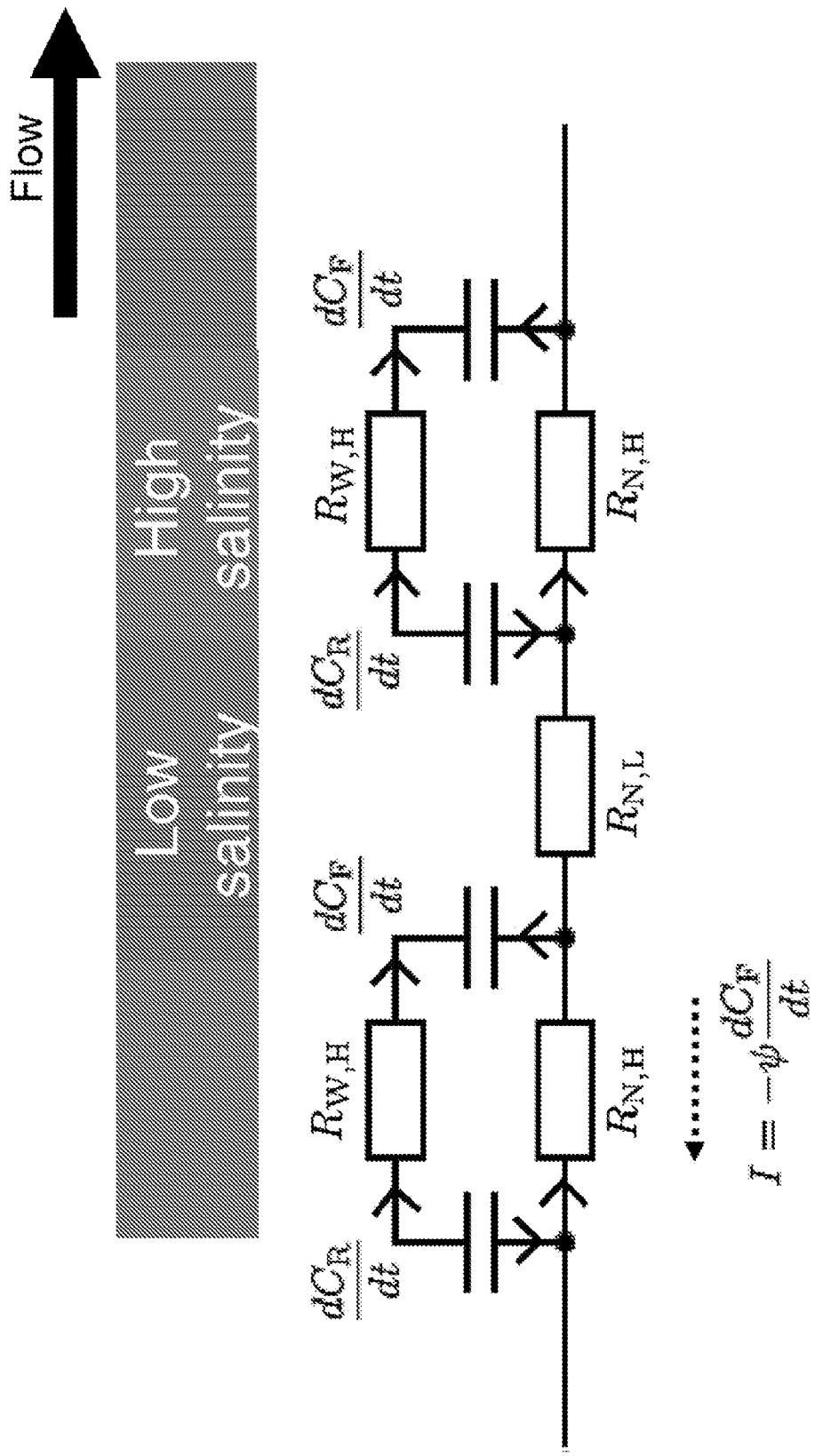
FIG. 18 depicts an equivalent circuit for the current induced in the system of liquid flow across the nanolayer with alternating high- and low-salinity segments. At the top, the alternating salinity of the liquid and flow direction are indicated. The liquid resistance to ion flow at low and high salinity are indicated by $R_{W,L}$ and $R_{W,H}$, respectively. The resistance to electron flow in the contact area between the nanolayer and water at low and high salinity are indicated by $R_{N,L}$ and $R_{N,H}$, respectively. The interfacial capacitance at the front and rear salinity boundaries ($C_F$ and $C_R$, respectively), which include contributions from the redox activity of the semiconducting metal oxide layer.

FIG. 18 presents the equivalent circuit for the current induced in the system of liquid flow across the nanolayer with alternating high- and low-salinity segments. The leftward electrical current in the nanofilm is generated by the relative motion of the ions (adsorption or desorption) that form the electrical double layer as the salinity gradient boundaries move.

FIG. 18 is closely related to the equivalent circuit presented for droplet motion on graphene in J. Yin et al., *Nature Nanotechnology* 9, 378-383 (2014), with two key distinctions. First, the current case is for liquid flow with alternating salinity. Second (and more important), the interfacial capacitance in the system presented here includes contributions from both the image charge formation in the metal layer as well as the large effect of electron transfer within the semiconducting metal oxide layer of the nanofilm surfaces.

Figure 19:
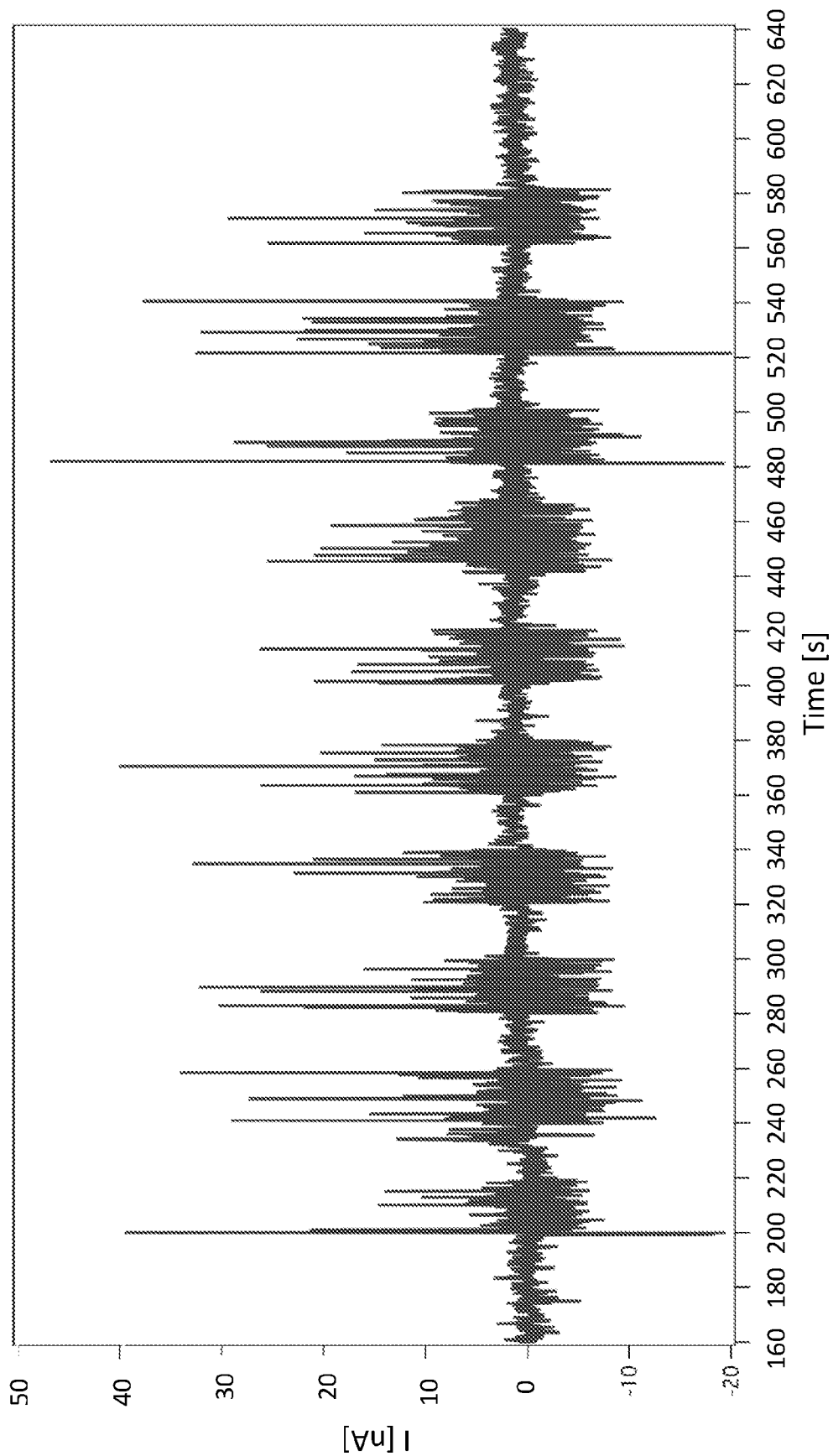
FIG. 19. Bunched current production recorded while flowing an aqueous solution of $YCl_3$ over a 10 nm thin iron nanolayer at a flow rate of 100 mL min$^{-1}$ using start-stop flow.

Example 2. This example illustrates a device the uses stop-flow operation to generate a time-varying current. An iron film having a thickness of 10 nm was used as the metal layer. An iron oxide overlayer formed spontaneously on the surface of the iron layer in air to a thickness of a few nm, as determined by XPS spectroscopy. An aqueous solution of $YCl_3$ was flowed over the amphoteric iron oxide that formed on the iron film at a flow rate of 100 mL/min for 20 seconds, followed by a 20 second pause in the flow, and then the resumption of the flow. As shown in FIG. 19, this generated in a time-varying current with an on-off pattern.

Figure 20:
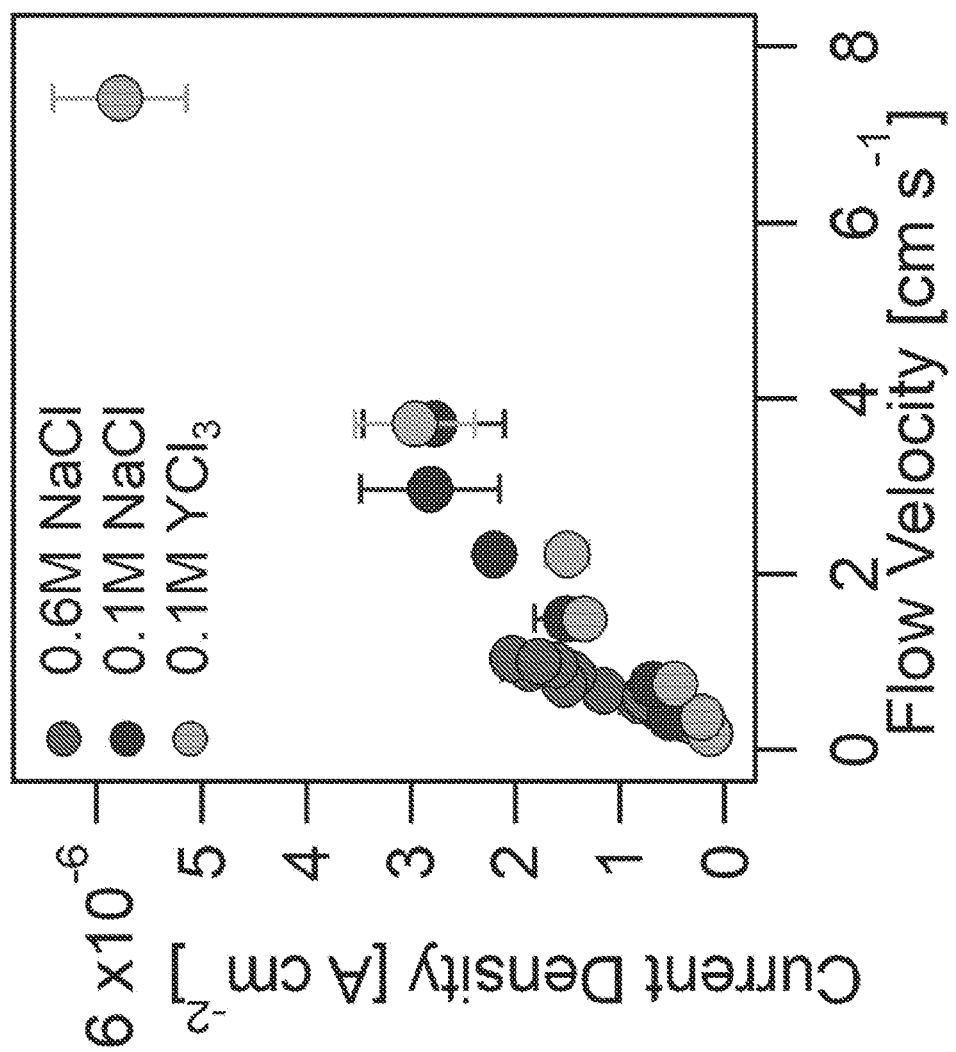
FIG. 20. Current produced using a 10 nm iron nanolayer when using a flow that alternated a 0.1 M aqueous solution of NaCl and $YCl_3$ with deionized water at various flow velocities.

Example 3. This example illustrates the use of an ionic solution that contains multivalent ions in the generation of an electronic current. An iron film having a thickness of 10 nm was used as the metal layer. An iron oxide overlayer formed spontaneously on the surface of the iron layer in air to a thickness of a few nm, as determined by XPS spectroscopy. Ionic solutions of the salt $YCl_3$ (0.1 M) in DI water were used. Ionic solutions of NaCl (0.1 M and 0.6 M) in DI water were used for comparison. Solutions of both salts produced a current in the iron layer when the salt solutions were flowed over the metal oxide surfaces over a range of flow rates, as shown in FIG. 20. These results demonstrate that mixtures of electrolytes comprised of a variety of different ions can be customized to serve the need of specific application endpoints.

Example 4. This example illustrates the utilization of a device as a pump by operating the device in reverse. A nickel film having a thickness of 20 nm coated onto a glass slide was used as the metal layer. A nickel oxide overlayer formed spontaneously on the surface of the nickel layer in air to a thickness of a few nm, as determined by XPS spectroscopy. A drop of 0.1 M salt solution was placed onto the surface of the nickel oxide tilted glass while the slide was in a tilted position. Applying a voltage across the salt solution resulted in the drop moving up the surface of nickel oxide, against gravity, indicating the device is doing work. Drops of deionized water showed no discernable movement when a voltage was applied in the same manner. This demonstrates that the device can be used as a silent and frictionless pump with no moving parts to move bodies of ionic solutions, including ocean water, bodily fluids (e.g., blood), or brines across a static surface.

Figure 21A:
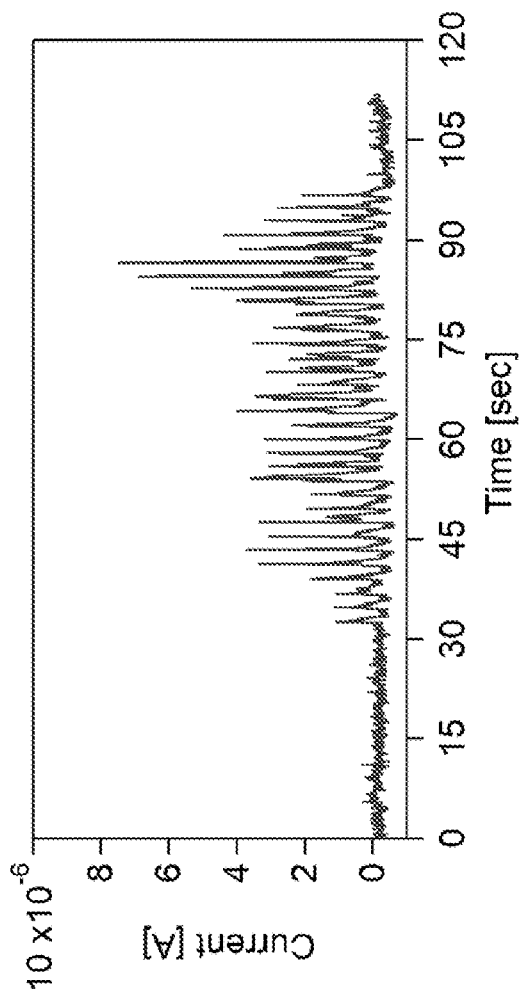
FIGS. 21A and 21B. Current (FIG. 21A) and voltage (FIG. 21B) obtained when moving a beaker of a 0.6 molar salt (NaCl) solution up and down over a stationary vertical metal nanolayer of amphoteric nickel oxide/nickel bilayer on glass, resulting in the regular, repeated wetting and dewetting of the metal oxide surface, repeated multiple times.
Figure 21B:
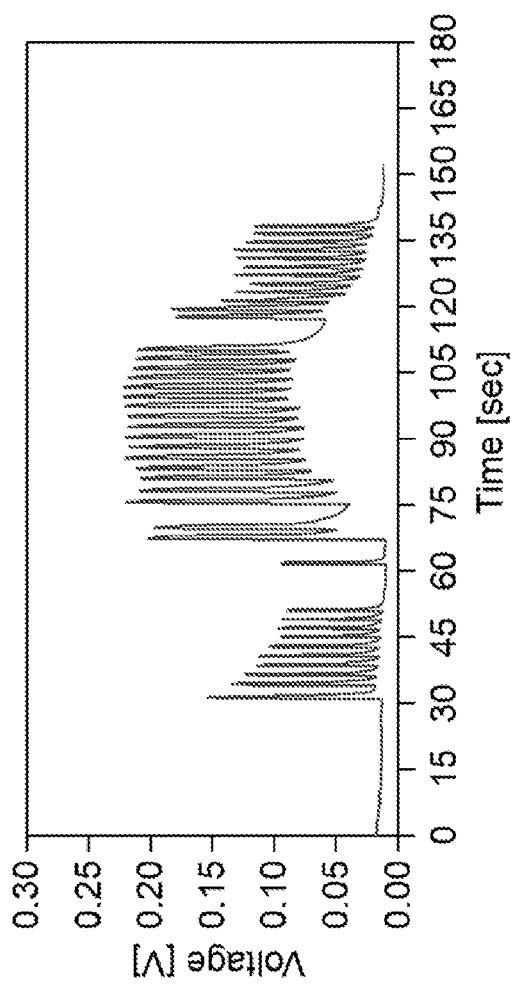

Example 5. This example illustrates the use of wave action to generate a varying current/voltage in a metal film. A nickel film having a thickness of 20 nm coated onto a glass slide was used as the metal layer. A nickel oxide overlayer formed spontaneously on the surface of the nickel layer in air to a thickness of a few nm, as determined by XPS spectroscopy. In order to simulate the expose of the nickel oxide surface to repeated wave action, the beaker of 0.6 M NaCl solution held in a beaker was repeatedly moved up and down over the surface of the stationary nickel oxide film while the glass slide was held vertically. As shown in FIG. 21A and FIG. 21B, this resulted in the regular, repeated wetting and dewetting of the metal oxide and resulted in a varying current and voltage in the nickel layer.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method of harvesting energy using a liquid flow-based device comprising:
    a metal layer comprising a metal;
    an amphoteric metal oxide film adjacent to the metal layer at an interface, the amphoteric metal oxide film having a surface disposed opposite the interface, wherein the metal layer has a thickness that facilitates charge carrier motion parallel to the interface; and
    at least one of: an electronic device that consumes electrical power connected laterally across the metal layer and configured to be powered by a current running parallel to the interface; and an energy storage device connected laterally across the metal layer and configured to be charged by a current running parallel to the interface, the method comprising:
    exposing the surface of the amphoteric metal oxide film to a flow of an ionic solution having a temporally varying flow rate, or a temporally varying flow direction, wherein the temporally varying flow rate or the temporally varying flow direction generates a current in the metal layer and the flow of the ionic solution does not have a temporally varying ionic conductivity; and
    powering the electronic device or charging the energy storage device with the generated current.

2. The method of claim 1, wherein the ionic solution is an aqueous salt solution.

3. The method of claim 2, wherein the ionic solution comprises salinized water from a natural body of water.

4. The method of claim 1, wherein the ionic solution comprises blood.

5. The method of claim 4, wherein the liquid flow-based device is implanted in a vein or an artery.

6. The method of claim 1, wherein the metal oxide is a redox active metal oxide comprising metal atoms in at least two different oxidation states.

7. The method of claim 6, wherein the metal is iron, nickel, copper, vanadium, or a mixture or alloy thereof.

8. The method of claim 1, wherein the metal oxide is extrinsically doped with an n-type or a p-type dopant.

9. The method of claim 1, wherein the metal layer has a thickness of up to 500 nm.

10. The method of claim 1, wherein the ionic solution comprises multivalent ions.

* * * * *